(12) United States Patent
Miller

(10) Patent No.: US 10,806,880 B2
(45) Date of Patent: Oct. 20, 2020

(54) RESPIRATORY APPARATUS

(75) Inventor: Andrew Miller, Bracknell (GB)

(73) Assignee: INTERSURGICAL AG, Vaduz (LI)

( * ) Notice: Subject to any disclaimer, the term of this patent is extended or adjusted under 35 U.S.C. 154(b) by 281 days.

(21) Appl. No.: 13/642,420

(22) PCT Filed: Apr. 19, 2011

(86) PCT No.: PCT/GB2011/050766
§ 371 (c)(1),
(2), (4) Date: Oct. 19, 2012

(87) PCT Pub. No.: WO2011/131974
PCT Pub. Date: Oct. 27, 2011

(65) Prior Publication Data
US 2013/0037026 A1 Feb. 14, 2013

(30) Foreign Application Priority Data
Apr. 19, 2010 (GB) .................... 1006480.6

(51) Int. Cl.
*A61M 16/04* (2006.01)
*A61M 16/06* (2006.01)
(Continued)

(52) U.S. Cl.
CPC ............ *A61M 16/04* (2013.01); *A61M 16/06* (2013.01); *A61M 16/0627* (2014.02);
(Continued)

(58) Field of Classification Search
CPC .............. A61M 16/04; A61M 16/0627; A61M 16/0816; A61M 16/06; A61M 16/12;
(Continued)

(56) References Cited

U.S. PATENT DOCUMENTS 4,029,093 A 6/1977 Kohnke
4,148,308 A * 4/1979 Sayer .................... A61B 1/24
128/207.14
(Continued)

FOREIGN PATENT DOCUMENTS

CN 1242711 A 1/2000
CN 101804033 A 12/2007
(Continued)

OTHER PUBLICATIONS

International Search Report and Written Opinion for PCT/GB2011/050766, dated Jul. 14, 2011, 5 pages.
(Continued)

*Primary Examiner* — Kendra D Carter
*Assistant Examiner* — Elliot S Ruddie
(74) *Attorney, Agent, or Firm* — Troutman Pepper Hamilton Sanders LLP (Rochester)

(57) ABSTRACT

A respiratory device for delivering gas to a patient comprises a gases passageway having proximal and distal ends, and a supplementary gas inlet in a side wall of the gases passageway. The supplementary gas inlet is adapted to direct gas along an interior surface of the gases passageway, such that the gas follows a generally helical path towards the distal end of the gases passageway.

23 Claims, 16 Drawing Sheets

(51) Int. Cl.
*A61M 16/08* (2006.01)
*A61M 16/12* (2006.01)

(52) U.S. Cl.
CPC ........ *A61M 16/0816* (2013.01); *A61M 16/12* (2013.01); *A61M 16/0434* (2013.01); *A61M 2202/0208* (2013.01); *A61M 2206/16* (2013.01)

(58) Field of Classification Search
CPC ...... A61M 16/0434; A61M 2202/0208; A61M 2206/16; A61M 16/042; A61M 16/0477; A61M 16/0486; A61M 16/122–127; A61M 2202/02; A61M 2206/00–10
USPC ............ 128/204.18, 203.26, 204.21, 205.24, 128/207.15, 207.14; 604/103.9, 526, 604/96.01
See application file for complete search history.

(56) References Cited

U.S. PATENT DOCUMENTS

| | | | |
|---|---|---|---|
| 4,189,101 A | | 2/1980 | Hughes |
| 4,265,237 A | | 5/1981 | Schwanbom et al. |
| 4,274,406 A | | 6/1981 | Bartholomew |
| 4,336,798 A | | 6/1982 | Beran |
| 4,416,273 A | * | 11/1983 | Grimes .................... 128/207.16 |
| 5,036,847 A | | 8/1991 | Boussignac et al. |
| 5,309,900 A | * | 5/1994 | Knoch .............. A61M 15/0086 128/200.14 |
| 5,538,002 A | | 7/1996 | Boussignac et al. |
| 5,775,320 A | * | 7/1998 | Patton ............... A61M 15/0065 128/200.14 |
| 6,138,668 A | | 10/2000 | Patton et al. |
| 6,273,087 B1 | | 8/2001 | Boussignac et al. |
| 6,516,801 B2 | | 2/2003 | Boussignac |
| 7,717,109 B2 | * | 5/2010 | Fukunaga et al. ....... 128/204.18 |
| 2003/0075176 A1 | | 4/2003 | Fukunaga et al. |
| 2004/0079364 A1 | * | 4/2004 | Christopher ...... A61M 16/0488 128/200.26 |
| 2004/0159321 A1 | * | 8/2004 | Eason ............... A61M 15/0028 128/203.15 |
| 2004/0194785 A1 | * | 10/2004 | Miller ............... A61M 16/0488 128/207.14 |
| 2009/0133697 A1 | | 5/2009 | Kwok et al. |

FOREIGN PATENT DOCUMENTS

| | | |
|---|---|---|
| EP | 0911051 A1 | 4/1999 |
| FR | 2392649 A1 | 3/1978 |
| JP | H09108354 A | 4/1997 |
| RU | 2144386 C1 | 1/2000 |
| TW | I281870 B | 1/2007 |
| WO | 2002056948 A1 | 7/2002 |

OTHER PUBLICATIONS

Great Britain Search Report for GB 1106550.5, dated Aug. 16, 2011, 2 pages.

* cited by examiner (a)

(b)

(c)

RESPIRATORY APPARATUS

This application is a national stage application under 35 U.S.C. § 371 of PCT Application No. PCT/GB2011/050766, filed Apr. 19, 2011, which claims the priority benefit of Great Britain Patent Application No. 1006480.6, filed Apr. 19, 2010.

FIELD OF THE INVENTION

This invention relates to respiratory apparatus, and in particular to improvements relating to the delivery of gases to a patient.

BACKGROUND OF THE INVENTION

Where it is desired to deliver gas to a patient, some form of interface device is typically used. The interface device may be invasive, i.e. extending into the airways of a patient. Devices adapted for this purpose include endotracheal tubes, laryngeal mask airways and other supraglottic airways. Alternatively, the interface device may be non-invasive, i.e. not extending into the airways of a patient, examples of which include respiratory masks, nasal cannula and nasal pillows. It is also common for supplementary gas to be delivered to a patient through invasive airway devices that are principally used to provide unobstructed respiration in a patient.

Invasive respiratory devices typically include a gases passageway that extends from a proximal end of the device located at the patient's mouth or nose, to a distal end of the device located within an airway of the patient, such as the larynx or trachea. These devices may be adapted for connection at their proximal end to apparatus for delivering inhalation gases to the patient, and possibly also removing exhalation gases from the patient. Alternatively, the respiratory devices may be adapted to be open to the atmosphere at their proximal end.

Where a therapeutic gas, such as oxygen, is to be delivered to a patient, it is usual to deliver the therapeutic gas to the proximal end of the device, either along the principal gases passageway, or through an additional inlet. A disadvantage of this arrangement is that the gases within the remainder of the device, i.e. between the proximal and distal ends, will be inhaled before any therapeutic gas is inhaled. The concentration of therapeutic gas inhaled by the patient is therefore relatively low.

A conventional arrangement for mitigating this problem involves introducing a catheter into the gases passageway of the device, such that the distal end of the catheter is in the region of the distal end of the airway device. The catheter is then used to deliver a therapeutic gas to the patient. However, this solution is not entirely satisfactory because the catheter partially obstructs the gases passageway of the device, and may cause trauma to the patient's airways during use.

Other attempts at mitigating this problem include the arrangements disclosed in U.S. Pat. Nos. 5,036,847 and 6,516,801. These arrangements involve the provision of gas conduits within the walls of the airway device, which deliver high speed jets of a gas to the distal end of the airway device. However, these arrangements are much more complex than conventional interface and airway devices, and hence costly to manufacture.

In addition, the arrangements disclosed in U.S. Pat. Nos. 5,036,847 and 6,516,801 have been used to generate continuous positive airway pressure (CPAP), for example in the gas inlet of a respiratory mask. In particular, the turbulence generated by the high speed jets of gas generates an airway pressure, which may remove the need for additional valves. However, these arrangements are also much more complex than conventional interface and airway devices, and hence costly to manufacture.

There have now been devised respiratory devices and connectors for delivering gas to a patient, which substantially overcome or mitigate some or all of the above-mentioned and/or other disadvantages associated with the prior art.

SUMMARY OF THE INVENTION

According to a first aspect of the invention, there is provided a respiratory device for delivering gas to a patient, the device comprising a gases passageway having proximal and distal ends, and a supplementary gas inlet in a side wall of the gases passageway, wherein the supplementary gas inlet is adapted to direct gas along an interior surface of the gases passageway, such that the gas follows a generally helical path towards the distal end of the gases passageway.

According to a further aspect of the invention, there is provided a method of delivering gas to a patient, which method comprises the steps of:
(a) providing a respiratory device for delivering gas to a patient, the device comprising a gases passageway having proximal and distal ends, and
(b) directing gas along an interior surface of the gases passageway, such that the gas follows a generally helical path towards the distal end of the gases passageway.

According to a further aspect of the invention, there is provided a respiratory device for delivering gas to a patient, the device comprising a gases passageway having proximal and distal ends, and a supplementary gas inlet in a side wall of the gases passageway, wherein the supplementary gas inlet is adapted to direct gas into an off-axis portion of the proximal end of the gases passageway, at an oblique angle to the longitudinal axis of the gases passageway, thereby generating helical flow within the gases passageway towards the distal end of the gases passageway.

The respiratory devices and method according to the present invention are advantageous principally because it has been found that gas directed along an interior surface of the device, such that the gas follows a generally helical path towards the distal end of the gases passageway, will travel a greater distance along the gases passageway before mixing with the other gases within the gases passageway, relative to prior art arrangements. The present invention therefore enables a gas to be introduced at a proximal region of the gases passageway, with the gas mixing with the other gases in the gases passageway when it reaches a distal region of the gases passageway.

The present invention is therefore particularly suitable for use with invasive respiratory devices. In particular, the invasive respiratory device may be provided with a supplementary gas inlet in a region of the device that is located externally of the patient during use, and the supplementary gas inlet may be adapted to direct gas along the gases passageway such that the gas follows a generally helical path towards the distal end of the gases passageway, and mixes with the other gases within the gases passageway in a region of the device that is located internally of the patient during use.

The present invention is therefore suitable for use with invasive respiratory devices adapted to act as interface devices, i.e. interfaces between respiratory apparatus and the patient, such as endotracheal tubes, laryngeal mask airways and supraglottic airways. The present invention is also suitable for use with invasive respiratory devices that are principally adapted to provide unobstructed respiration in a patient, i.e. airway devices, such as Guedel airways and tracheotomy tubes.

The concentration of the gas introduced through the supplementary gas inlet that is inhaled by the patient may therefore be increased, in particular the so-called "dead space" within the respiratory device may be reduced. Furthermore, the respiratory device according to the present invention does not require ancillary devices, such as catheters, to be introduced into the gases passageway, nor does it require complex arrangements such as gas conduits in the wall of the airway device, as in prior art arrangements.

The present invention is also suitable for use with non-invasive respiratory devices in which it is advantageous to provide mixing of gases in a region of the gases passageway that is remote from the supplementary gas inlet. In particular, the gas introduced through the supplementary gas inlet may be adapted to mix with the other gases within the gases passageway in a region of the device in which it is not possible, or desirable, to provide a gas inlet. In addition, as discussed in more detail below, the present invention may be utilised in a non-invasive respiratory device in order to provide Positive End Expiratory Pressure (PEEP) and/or Continuous Positive Airway Pressure (CPAP). Examples of non-invasive respiratory devices are respiratory masks, nasal cannula and nasal pillows.

It is thought that the combination of the momentum of the gas introduced through the supplementary gas inlet, and the centripetal force applied by the interior surface of the airway device, acts to maintain the flow of gas in a radially outer region of the gases passageway, until the momentum of the gas reduces sufficiently for the gas flow to become turbulent in a radially inner region of the gases passageway, thereby causing mixing of the gas with the other gases in the gases passageway.

The "other gases in the gases passageway" will typically be the gases that are supplied through the proximal end of the gases passageway, either from the respiratory apparatus to which the device is connected or from the atmosphere, and the gases that are exhaled by the patient. It is thought that these "other gases" form a principal flow in an inner region of the gases passageway, with the gas introduced through the supplementary gas inlet flowing in a radially outer region of the gases passageway, until mixing occurs.

The respiratory device according to the present invention is particularly suitable for use in oxygen therapy. In particular, the supplementary gas inlet may be connected to a supply of oxygen, such that a flow of oxygen follows a helical path towards the distal end of the gases passageway, in use. The oxygen may therefore mix with the other gases within the gases passageway in a distal region of the gases passageway, thereby increasing the concentration of oxygen inhaled by the patient relative to prior art devices.

The respiratory device may be adapted for connection to a breathing circuit at the proximal end of the gases passageway. Alternatively, the gases passageway may be adapted to be open to the atmosphere at its proximal end, such as in the case of an airway device. In these embodiments, the supplementary gas inlet may be closed when the respiratory device is connected to a breathing circuit, such as an anaesthetic breathing circuit, or the respiratory device is open to the atmosphere at its proximal end. However, where it is desired to provide the patient with a therapeutic gas, such as oxygen, a supply of that gas may be connected to the supplementary gas inlet and delivered to the patient, as described above. For example, such devices are particularly suitable for post-operative oxygen therapy.

Since the respiratory device according to the invention may be used to provide a turbulent region of a gas, such as oxygen, at a relatively high concentration in a distal region of the gases passageway, the airway device is also particularly advantageous for use in passive oxygenation. In particular, where a patient is not breathing, a supply of oxygen may be connected to the supplementary gas inlet of the respiratory device according to the invention, and delivered to the patient. It has been found that a turbulent flow of oxygen in a distal region of the gases passageway, as provided by the present invention, may promote gas exchange between the airway device and the lungs of the patient more effectively than simple Brownian gas diffusion. This may be particularly advantageous in resuscitation.

It has also been found that where high flow rates of gas, such as oxygen, are supplied to the supplementary gas inlet, the turbulent flow generated when the gas mixes with the other gases in the gases passageway provides a resistance to exhalation and/or inhalation of the patient, and may therefore provide Positive End Expiratory Pressure (PEEP) and/or Continuous Positive Airway Pressure (CPAP). This PEEP/CPAP may be relatively low, but may be adapted to be sufficient to keep the lungs of the patient at least partially inflated, and also increase the efficiency of gas exchange. Indeed, the present invention provides an arrangement for generating PEEP/CPAP that is much simpler, and hence less costly to manufacture, than prior art arrangements.

It has been found that PEEP/CPAP may be generated when the flow rate through the supplementary gas inlet is sufficiently high, for a given size of exit orifice of the supplementary gas inlet. This means that a particular respiratory device may provide PEEP/CPAP when the flow rate through the gas inlet is above a threshold rate. In particular, it has been found that were the exit orifice is approximately 0.8 mm in diameter, PEEP/CPAP may be provided when the flow rate through the supplementary gas inlet is approximately 15 litres per minute or above. Hence, where PEEP/CPAP is not required, the flow rate may be reduced to approximately 10 litres per minute, for example.

The supplementary gas inlet preferably comprises a proximal end adapted to be connected to a supply of gas, and a distal end in fluid communication with an exit orifice in the side wall of the gases passageway. The supplementary gas inlet is preferably adapted to supply gas to the exit orifice, such that a jet of gas is directed along an interior surface of the gases passageway. The area of the exit orifice is preferably less than the area of the proximal end of the supplementary gas inlet, such that the supplementary gas inlet increases the velocity of the gas flowing through the exit orifice.

The supplementary gas inlet preferably directs gas into an off-axis portion of the gases passageway, at an oblique angle to the longitudinal axis of the gases passageway, in order to generate helical flow within the gases passageway. The supplementary gas inlet preferably directs gas into the gases passageway at an angle to the longitudinal axis of the gases passageway of between 10° and 80°, more preferably between 30° and 60°, for example approximately 45°.

The supplementary gas inlet preferably projects from the side wall of the gases passageway, in a direction that is parallel to, but offset from, an axial plane 721 of the portion of the gases passageway in which the supplementary gas inlet is formed. The supplementary gas inlet preferably also projects from the gases passageway at an oblique angle to the portion of the gases passageway in which the supplementary gas inlet is formed, in the direction of the proximal end of the gases passageway. According to a further aspect of the invention, there is provided a respiratory device for delivering gas to a patient, the device comprising a gases passageway having proximal and distal ends, and a supplementary gas inlet in a side wall of the gases passageway, wherein the supplementary gas inlet projects from the side wall of the gases passageway, in a direction that is parallel to, but offset from, an axial plane 721 of the portion of the gases passageway in which the supplementary gas inlet is formed, and the supplementary gas inlet also projects from the gases passageway at an oblique angle to the portion of the gases passageway in which the supplementary gas inlet is formed, in the direction of the proximal end of the gases passageway.

The area of the exit orifice is preferably significantly smaller than the internal cross-sectional area of the gases passageway. In particular, the diameter of the exit orifice is preferably in the range of 0.2 to 3 mm, more preferably in the range of 0.4 to 2 mm, and most preferably in the range of 0.6 to 1.2 mm. The internal diameter of the gases passageway will typically be in the range of 10-25 mm, e.g. approximately 15 mm.

The size of the exit orifice is preferably selected to achieve the desired range of the helical flow within the gases passageway, which will also be determined by the internal diameter of the gases passageway and the rate of flow of gas through the exit orifice. In particular, it has been found that an exit orifice of between 0.6 and 1.2 mm would be suitable where the internal diameter of the gases passageway is approximately 15 mm, and the gas flow rate is in the range of 5-15 $lm^{-1}$.

Where the respiratory device is an invasive interface device, such as a laryngeal mask airway or an endotracheal tube, the distal end of the gases passageway is preferably adapted to be in sealed engagement with an airway of the patient, such as the laryngeal inlet or the trachea. Hence, in these embodiments, the respiratory device preferably includes a sealing member at its distal end, which has an exterior shape that is readily deformable into a shape matches that of the internal surface of the airway of the patient with which the sealing member will engage. For example, where the respiratory interface device is an endotracheal tube, the exterior surface of the sealing member preferably has a substantially circular or elliptical cross-sectional shape, before use. Such a sealing member is commonly referred to as a "cuff".

The proximal end of the gases passageway may simply be adapted to be in fluid communication with the atmosphere, such that atmospheric air is inhaled by the patient, and the patient's exhalation gases pass into the atmosphere, during use. However, where the respiratory device is an interface device, the proximal end of the gases passageway is adapted to be connected to respiratory apparatus, such as a breathing circuit. Hence, in these embodiments, the respiratory device preferably includes a connector at the proximal end of the gases passageway. Most preferably, the supplementary gas inlet is formed integrally with the connector, i.e. the connector and the supplementary gas inlet may be formed as a unitary component, e.g. by single-shot injection moulding.

The gases passageway preferably has a form suitable for maintaining the helical flow of gas for the desired distance. In particular, the gases passageway preferably has a generally circular cross-section, and preferably has a generally constant cross-section, at least along that portion of the gases passageway in which it is desired to maintain a helical flow of gas from the supplementary gas inlet, in use. The interior surface of the gases passageway is preferably substantially smooth. However, the interior surface of the gases passageway may include formations that promote turbulent flow in a distal region of the gases passageway, if desired, which may take the form of projections and/or recesses in the interior surface.

Where the respiratory device is invasive, the gases passageway of the respiratory device is preferably sufficiently deformable to facilitate insertion into a patient's airway. However, in these embodiments, the respiratory device preferably includes a connector at the proximal end of the gases passageway, with the supplementary gas inlet projecting from a side wall thereof. The connector may therefore be formed of a more rigid material than the remainder of the gases passageway, in order to facilitate connection to a breathing circuit and/or a source of gas.

Indeed, a connector for respiratory apparatus that includes a supplementary gas inlet projecting from a side wall may be supplied separately for use with conventional respiratory devices.

According to a further aspect of the invention, there is provided an adaptor for use with a respiratory device for delivering gas to a patient, the adaptor comprising a gases passageway adapted for connection to a proximal end of a gases passageway of the respiratory device, and a supplementary gas inlet in a side wall of the gases passageway of the adaptor, wherein the supplementary gas inlet is adapted to direct gas along an interior surface of the gases passageway of the adaptor and/or the airway device, such that the gas follows a generally helical path towards a distal end of the gases passageway of the respiratory device.

The respiratory device may be any of the types of respiratory devices discussed above in relation to the previous aspects of the invention. The adaptor preferably comprises a tubular connector adapted for engagement with the proximal end of the airway device, and preferably also a tubular connector adapted for connection to respiratory apparatus. The gases passageways of the adaptor and the respiratory device are preferably co-axial, i.e. in registration, and preferably have the same cross-sectional shape and dimensions. In particular, the gases passageway of the respiratory device may include a recess adapted to accommodate the tubular connector of the adaptor, such that the interior surface of the combined adaptor and respiratory device arrangement is sufficiently smooth not to affect the helical flow of gas during use. Alternatively, the tubular connector of the adaptor may be a female connector, in which case the gases passageway of the adaptor may include a recess adapted to accommodate the tubular connector of the respiratory device.

The adaptor is preferably formed as a unitary component, e.g. by single-shot injection moulding.

By "generally helical path" is meant a path that has a generally circular component, and a generally axial component. In particular, the angle of the path relative to the axis of the gases passageway will vary depending upon the flow of other gases within the gases passageway, as well as the momentum of the gas flow itself, as illustrated in relation to the specific embodiments described below.

The respiratory device and adaptor discussed above are preferably each formed of plastics material. The adaptor is preferably formed as a unitary component. Similarly, the respiratory device preferably includes a connector, which is formed as a unitary component. The respiratory device may include other components, such as a gases passageway component, which may be formed of a different material to the connector, for example a softer material to reduce the risk of trauma to the patient.

BRIEF DESCRIPTION OF THE DRAWINGS

A preferred embodiment of the invention will now be described in greater detail, by way of illustration only, with reference to the accompanying drawings, in which

FIG. 5a is a perspective view of a Guedel airway according to the invention;

FIG. 5b is a front view of the Guedel airway of FIG. 5a;

FIG. 5c is a cross-sectional view of the Guedel airway of FIG. 5a;

DETAILED DESCRIPTION OF THE INVENTION

Figure 1:
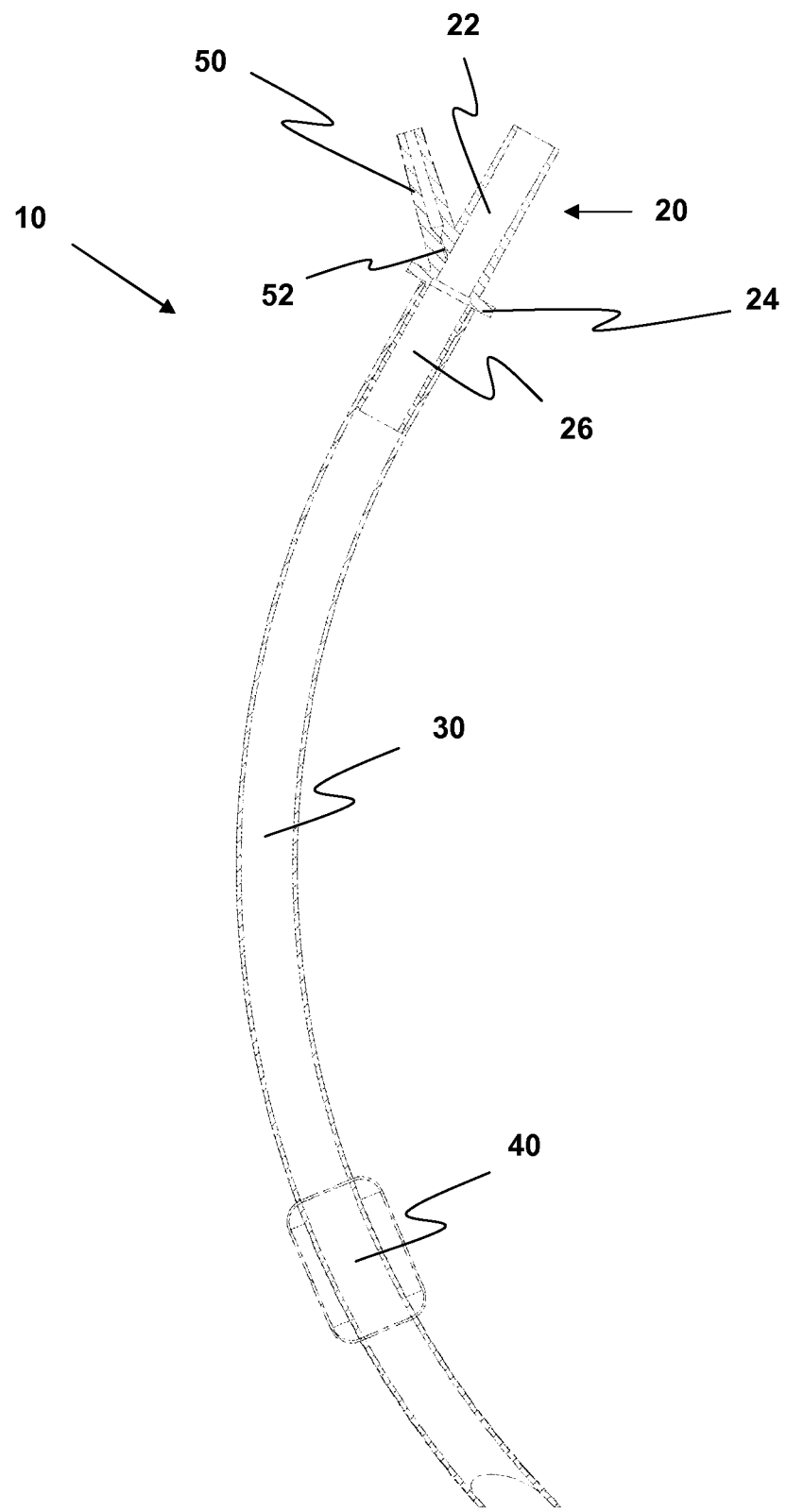
FIG. 1 is a cross-sectional view of a first embodiment of an endotracheal tube according to the invention.

FIG. 1 shows a first embodiment of an endotracheal tube according to the invention, which is generally designated 10. The endotracheal tube 10 comprises a connection component 20, an airway tube 30 and a sealing member 40. The endotracheal tube 10 is adapted to be inserted into the airways of a patient, through the mouth, such that the connection component 20 projects from the patient's mouth, and the sealing member 40 is accommodated within the trachea of the patient.

The airway tube 30 is a generally flexible tube, which defines a gases passageway of substantially constant circular cross-section, which is engaged with the connection component 20 at its proximal end. The sealing member 40 surrounds a portion of the airway tube 30, close to its distal end. The internal and external diameters of the airway tube 30 are chosen to correspond to the size of the patient, e.g. adult or pediatric.

The connection component 20 comprises a male tubular connector 22 suitable for connection to a conventional breathing circuit, and a co-axial engagement member 26 that is received within the proximal end of the airway tube 30 with a close fit. The connector 22 and the engagement member 26 together define a gases passageway of substantially constant circular cross-section. An outwardly projecting support flange 24 is provided between the connector 22 and the engagement member 26, which abuts the end of the airway tube 30.

The sealing member 40 is sized and shaped to correspond to the trachea of a patient. In use, the distal end of the airway tube is inserted into the mouth of a patient and into the trachea. The sealing member is adapted to form an effective seal with the trachea of the patient.

The connection component 20 is formed of a substantially rigid material, such as polypropylene. The airway tube 30 however, is integrally formed of a material that is softer and more deformable, in order to reduce the risk of trauma to the patient, but still sufficiently rigid to prevent collapse of the airway tube 30 during use.

The oxygen inlet 50 has the form of a generally cylindrical tube, which projects from the connection component 20, and is adapted for connection to a supply of oxygen. In particular, the oxygen inlet 50 projects from the wall of the connector 20, from a position adjacent to the support flange 24, and offset from a medial plane of the device. The oxygen inlet 50 extends at an angle of approximately 45° to the connector 22, in the direction of the proximal end of the connector 22.

The interior of the oxygen inlet 50 forms a gases passageway with a substantially constant cross-section, but which reduces in diameter as it approaches the wall of the connector 22 and terminates a small exit orifice 52. In particular, the exit orifice 52 has a diameter of approximately 0.8 mm, which has been found to be effective for a gases passageway through the device of approximately 15 mm diameter. The oxygen inlet 50 has a slightly tapered exterior that facilitates connection to the supply of oxygen.

The oxygen inlet 50 is adapted to direct a jet of oxygen through the exit orifice 52, into the gases passageway of the endotracheal tube 10. The jet of oxygen is directed circumferentially along the internal surface of the connection component 20, but also at an angle of approximately 45° to the principal direction of flow through the gases passageway of the endotracheal tube 10, thereby causing the jet of oxygen to follow a helical path along the gases passageway towards the distal end.

The orientation of the oxygen inlet 50 and the size of the exit orifice 52 cause oxygen to be introduced into the gases passageway of the device 10 in a manner that provides substantial advantages over the prior art. In particular, it has been found that the oxygen introduced through the oxygen inlet 50 mixes with the other gases in the gases passageway of the device further along the gases passageway, and in particular closer to the distal end of the gases passageway, than in prior art arrangements.

It is presently thought that the flow of oxygen, in use, in the endotracheal tube 10 occurs along the lines of that schematically illustrated in FIGS. 2a to 2c in relation to a second embodiment of an endotracheal tube according to the invention, and described in more detail below.

Figure 2A:
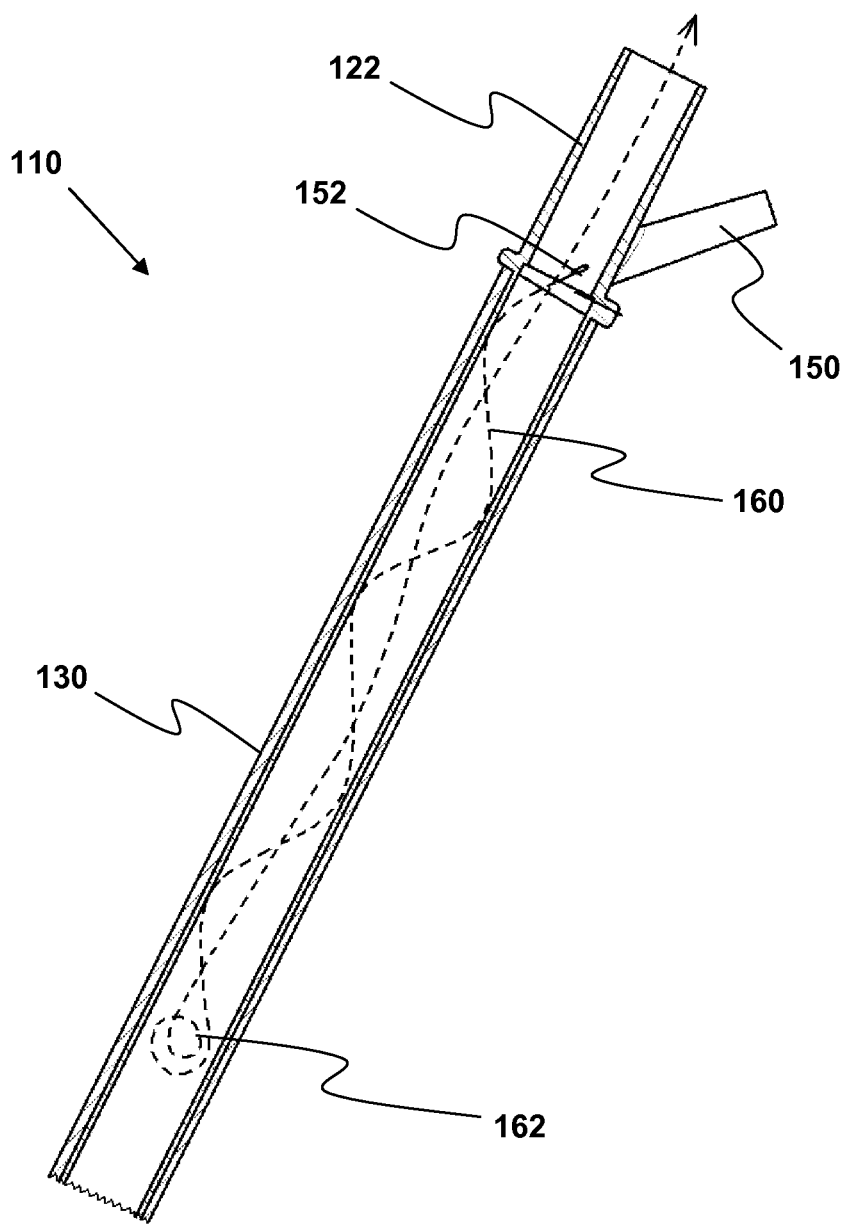
FIG. 2a is a fragmentary cross-sectional view of a second embodiment of an endotracheal tube according to the invention, which includes a schematic illustration of airflow within the device during use.
Figure 2B:
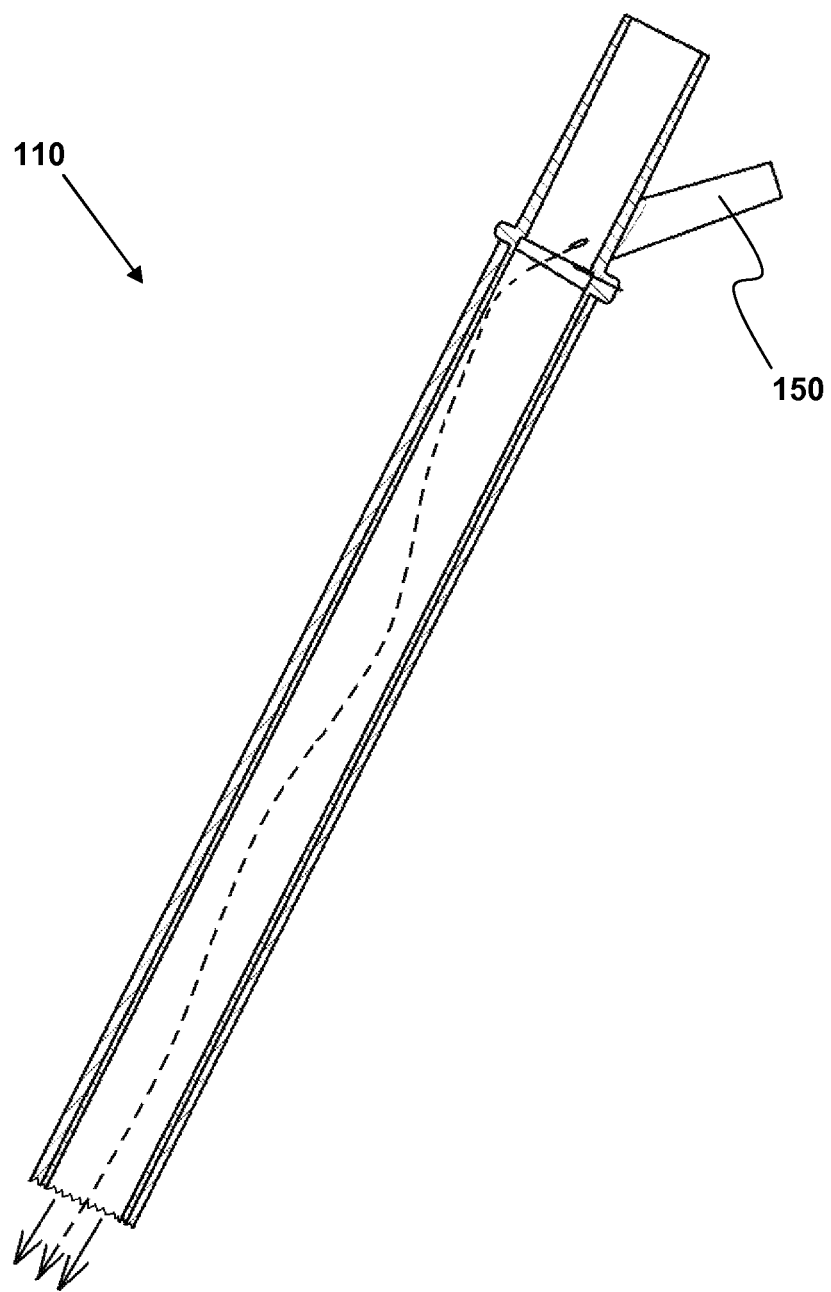
FIG. 2b is a view similar to FIG. 2a, which includes a schematic illustration of airflow within the endotracheal tube during inhalation.
Figure 2C:
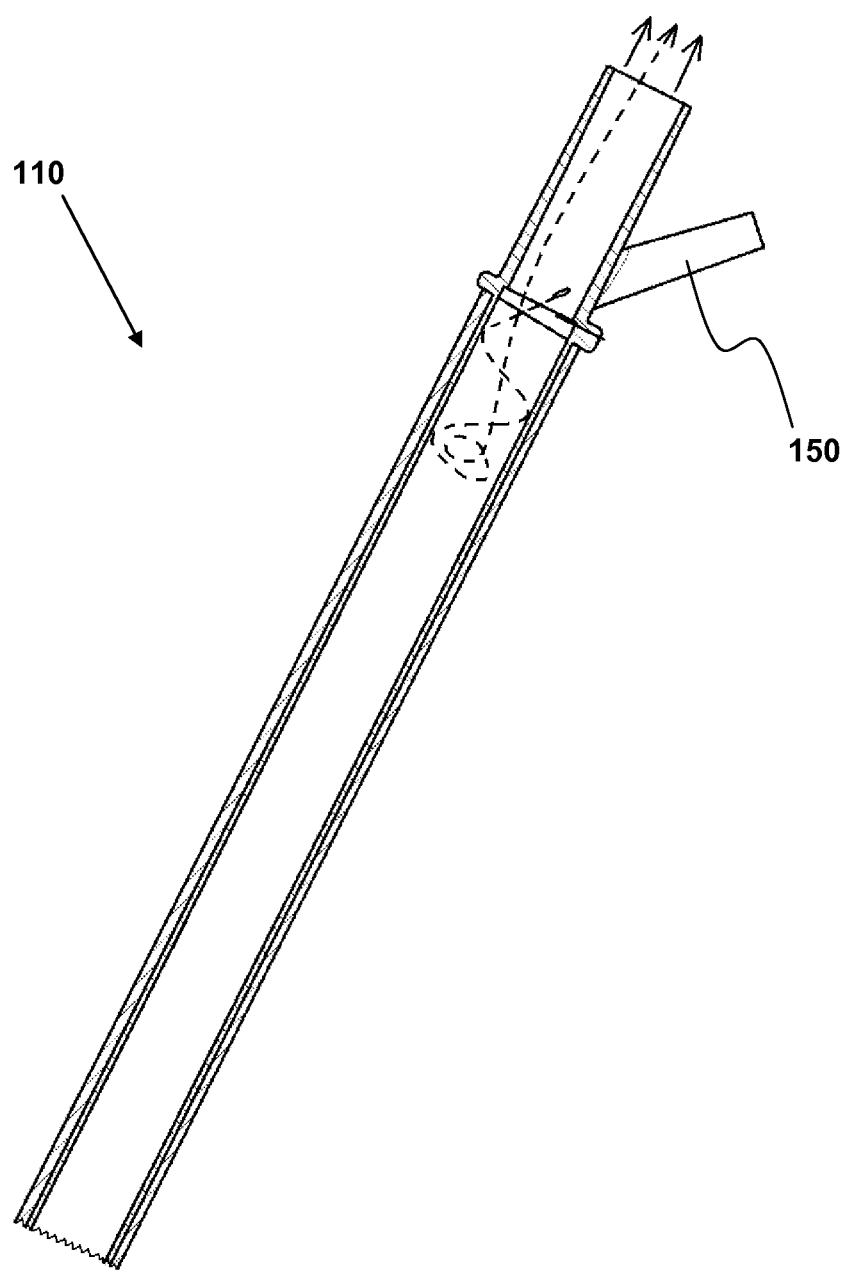
FIG. 2c is a view similar to FIG. 2a, which includes a schematic illustration of airflow within the endotracheal tube during exhalation.

FIGS. 2a to 2c show a proximal end portion of a second embodiment of an endotracheal tube according to the invention, which is generally designated 110, as well as schematic illustrations of the flow of oxygen that is thought to occur when oxygen is introduced through the oxygen inlet 150 during use.

The endotracheal tube 110 shown in FIGS. 2a to 2c comprises a connector 122 at its proximal end, and an airway tube 130 that extends into a patient's trachea during use. The connector 122 has the same form as the connector 120 described above in relation to FIG. 1. In particular, the connector includes an oxygen inlet 150. The oxygen inlet 150 is adapted to introduce a jet of oxygen into the endotracheal tube 110, such that the jet of oxygen is directed along the interior surface of the otherwise conventional endotracheal tube 110.

FIG. 2a shows a schematic illustration of the flow of the oxygen introduced through the oxygen inlet 150 into the gases passageway of the endotracheal tube 110, from entry as a jet 160 through the exit orifice 152 to eventual exit through the connector 122 of the endotracheal tube 110. In particular, the flow of oxygen shown in FIG. 2a is that flow that is expected when there is no overall flow of other gases through the gases passageway of the endotracheal tube 110.

As shown in FIG. 2a, a jet of oxygen 160 is directed by the oxygen inlet 150 along the interior surface of the endotracheal tube 110, at an angle of approximately 45° to the central axis of the gases passageway. The jet of oxygen 160 initially has a linear path, but a centripetal force is imparted by the interior surface of the endotracheal tube 110, which causes the jet of oxygen 160 to travel along a generally helical path. It is thought that the combination of the momentum of the jet of oxygen 160 introduced through the gas inlet 150, and the centripetal force applied by the interior surface of the endotracheal tube 110, acts to maintain the helical flow of oxygen in a radially outer region of the gases passageway.

As the jet of oxygen 160 travels along the gases passageway of the endotracheal tube 110, it gradually loses momentum until its momentum is no longer sufficient to maintain the helical flow of oxygen in a radially outer region of the gases passageway. The flow of oxygen will then become turbulent in a radially inner region of the gases passageway, thereby causing mixing of the oxygen with the other gases in the gases passageway in a region of turbulent flow 162. The oxygen will then be carried out of the endotracheal tube 110, through the airway tube 130 and the connector 122 at the proximal end, with the other gases in the gases passageway, due to the increased pressure caused by the introduction of oxygen through the oxygen inlet 150.

FIG. 2b shows a schematic illustration of the flow of the oxygen introduced through the oxygen inlet 150, into the endotracheal tube 110, during inhalation. In particular, the flow of other inhalation gases towards the patient, through the gases passageway of the endotracheal tube 110, will cause the oxygen to lose momentum less quickly, and hence maintain a helical flow of the oxygen for a greater distance along the gases passageway. Hence, the flow of oxygen will not become turbulent until closer to the patient during inhalation.

FIG. 2c shows a schematic illustration of the flow of the oxygen introduced through the oxygen inlet 150, into the endotracheal tube 110, during exhalation. In particular, the flow of exhalation gases away from the patient, through the gases passageway of the endotracheal tube 110, will cause the oxygen to lose momentum significantly quicker. The flow of oxygen will therefore become turbulent in a radially inner region of the gases passageway that is much closer to the proximal end of the endotracheal tube 110 than during inhalation (FIG. 2b) or in static conditions (FIG. 2a).

It has also been found that where high flow rates of oxygen are supplied to the gas inlet 150, the turbulent flow generated when the gas mixes with the other gases in the gases passageway provides a resistance to exhalation of the patient, and may therefore provide Positive End Expiratory Pressure (PEEP) and/or Continuous Positive Airway Pressure (CPAP). This PEEP/CPAP may be relatively low, but may be adapted to be sufficient to keep the lungs of the patient at least partially inflated, and also increase the efficiency of gas exchange.

PEEP/CPAP is generated when the flow rate through the gas inlet 150 is sufficiently high, for a given size of exit orifice 152. This means that this endotracheal tube 110 will provide PEEP/CPAP when the flow rate through the gas inlet 150 is above a threshold rate. In particular, this endotracheal tube 110 has an exit orifice 152 of approximately 0.8 mm diameter, and it has been found that PEEP/CPAP is provided when the flow rate is approximately 15 litres per minute and above. Hence, where PEEP/CPAP is not required, the flow rate may be reduced to approximately 10 litres per minute, for example.

Figure 3:
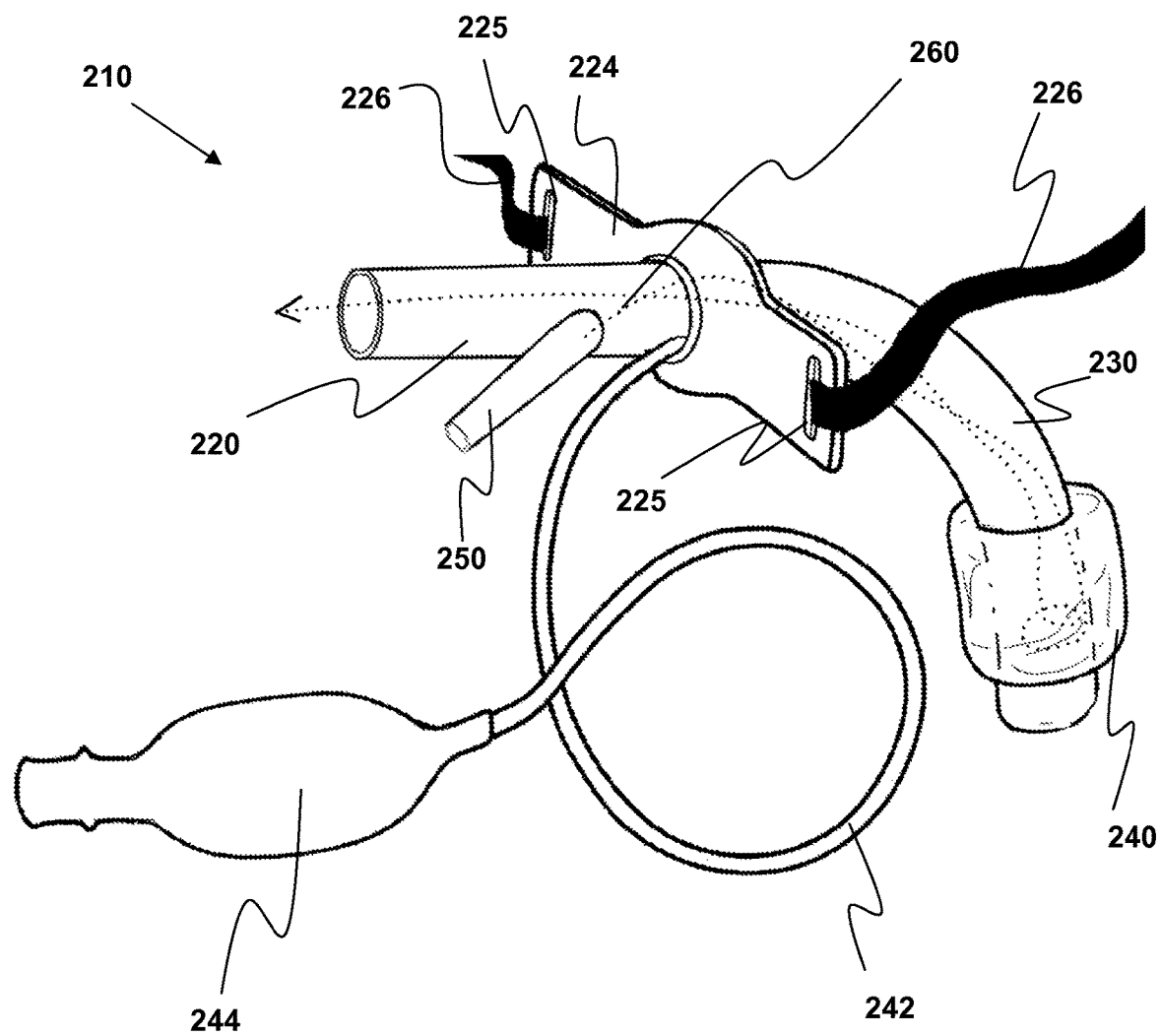
FIG. 3 is a schematic view of a tracheotomy tube in accordance with the invention.

FIG. 3 shows a tracheotomy tube according to the invention, which is generally designated 210. The tracheotomy tube 210 comprises a gases passageway 230, which is arcuate in form. The gases passageway 230 includes a connector 220 at one end that is adapted to connect the tracheotomy tube 210 to a breathing circuit. The tracheotomy tube 210 also includes an elongate flange 224, which is disposed adjacent to the connector 220. The flange 224 includes an opening 225 at each end for engagement with a strap 226, which secures the tracheotomy tube 210 to the patient.

At the other end of the tubular passageway 230, an inflatable cuff 240 surrounds a portion of the gases passageway 230. The inflatable cuff 240 has a circular cross-section, and an external surface that is generally convex in form along its longitudinal axis. The inflatable cuff 240 is connected to a hand-pump 244 by a connecting tube 242.

The tracheotomy tube 210 is generally used as an emergency measure when a patient is unable to breathe. An incision is then made into the trachea of the patient, into which the distal end of the tracheotomy tube 210 is inserted. Once the distal end is located in the trachea, the hand-pump 244 is operated to introduce air into the inflatable cuff 240 to inflate it in order to ensure a good seal between the gases passageway 230 and the interior wall of the trachea. The strap 226 may be tied around the neck of the patient to stabilize the tube 210.

In contrast to a conventional tracheotomy tube, the tracheotomy tube 210 also includes an oxygen inlet 250, which has a similar arrangement to the oxygen inlets 50,150 of the endotracheal tubes 10,110 described above. In particular, the oxygen inlet 250 is adapted to direct a jet of oxygen into the gases passageway 230 of the tracheotomy tube 210. The jet of oxygen is directed circumferentially along the internal surface of the connector 220, but also at an angle of approximately 45° to the principal direction of flow through the gases passageway 230 of the tracheotomy tube 210, thereby causing the jet of oxygen to follow a helical path along the gases passageway 230 towards the distal end.

The arrangement of the oxygen inlet 250 causes oxygen to be introduced into the gases passageway 230 of the tracheotomy tube 210 in a manner that provides substantial advantages over the prior art. In particular, it has been found that the oxygen introduced through the oxygen inlet 250 mixes with the other gases in the gases passageway of the tracheotomy tube 210 further along the gases passageway 230, and in particular closer to the distal end of the gases passageway 230, than in prior art arrangements.

For example, FIG. 3 includes a schematic illustration of the flow of oxygen that is thought to occur when oxygen is introduced through the oxygen inlet 250 during use. In particular, FIG. 3 illustrates the flow of the oxygen introduced through the oxygen inlet 250 into the gases passageway of the tracheotomy tube 210, from entry as a jet 260 to eventual exit through the connector 220 of the tracheotomy tube 210.

In addition, the helical flow of oxygen will become turbulent at a distal end of the gases passageway 230 of the tracheotomy tube 210, thereby causing mixing of the oxygen with other gases in the gases passageway 230. It has been found that this turbulent mixing of the oxygen with the other gases in the gases passageway may provide Positive End Expiratory Pressure (PEEP) and/or Continuous Positive Airway Pressure (CPAP). This PEEP/CPAP may be relatively low, but may be adapted to be sufficient to keep the lungs of the patient at least partially inflated, and also increase the efficiency of gas exchange.

PEEP/CPAP is generated when the flow rate through the gas inlet 250 is sufficiently high, for a given size of exit orifice. This means that this tracheotomy tube 210 will provide PEEP/CPAP when the flow rate through the gas inlet 250 is above a threshold rate. In particular, this tracheotomy tube 210 has an exit orifice of approximately 0.8 mm diameter, and it has been found that PEEP/CPAP is provided when the flow rate is approximately 15 litres per minute and above. Hence, where PEEP/CPAP is not required, the flow rate may be reduced to approximately 10 litres per minute, for example.

Figure 4A:
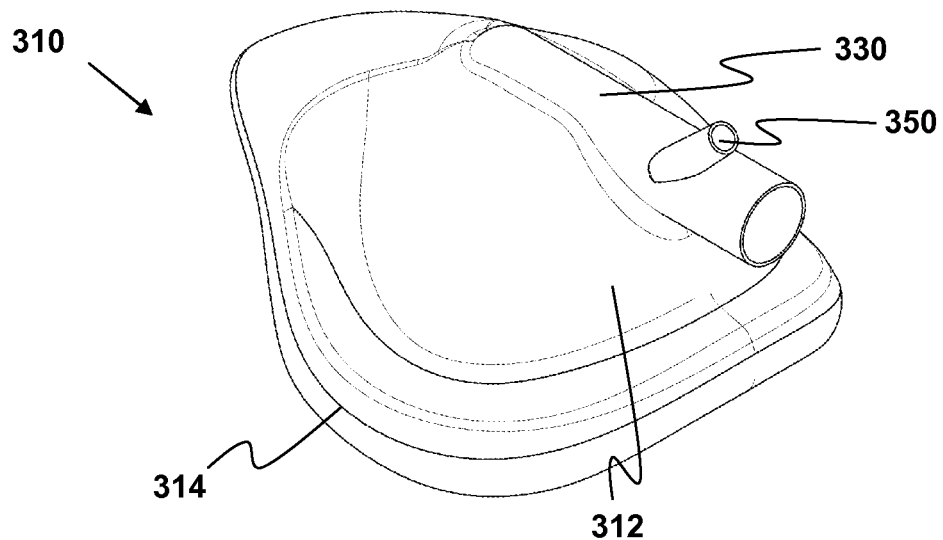
FIG. 4a shows a perspective view of a respiratory mask according to the invention.
Figure 4B:
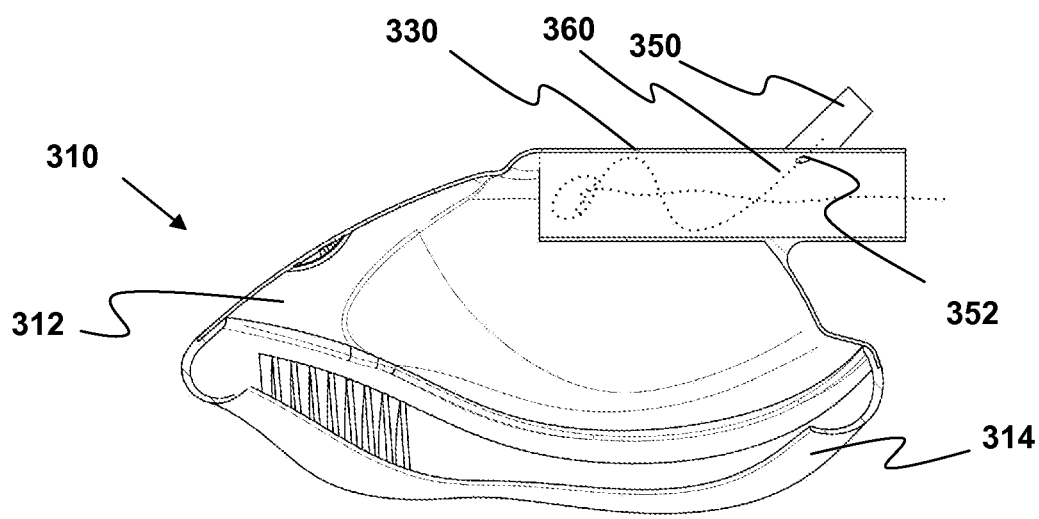
FIG. 4b shows a side view of the respiratory mask of FIG. 4a, which includes a schematic illustration of airflow within the device during use.

FIGS. 4a and 4b show a respiratory mask according to the invention, which is generally designated 310. The respiratory mask 310 comprises a mask body 312 for covering the mouth and nose of the patient, and defining a cavity from which the patient inhales. The mask body is formed from relatively rigid plastics material, such as polypropylene, but includes a more flexible sealing member 314 at its periphery for contacting the patient's face, when fitted. A gases passageway 330 projects from the mask body 312 from a position close to its centre. The gases passageway 330 comprises a short, generally inflexible tube of substantially circular cross-section. At one end, the gases passageway 330 is in fluid communication with the interior of the mask body 312. At the other end, the gases passageway 330 is adapted for connection to a conventional breathing circuit.

In contrast to a conventional respiratory mask, the gases passageway 330 also includes an oxygen inlet 330 in the form of a generally cylindrical tube, which projects from the wall of the gases passageway 330 in a similar manner to the manner in which oxygen inlets 50,150,250 project from the walls of the connectors 20,120,220 in the endotracheal tubes and the tracheotomy tube described above.

The oxygen inlet 350 is adapted to direct a jet of oxygen through an exit orifice 352, into the gases passageway 330. The jet of oxygen is directed circumferentially along the internal surface of the gases passageway 330, but also at an angle of approximately 45° to the principal direction of flow through the gases passageway 330, thereby causing the jet of oxygen to follow a helical path along the gases passageway 330 towards the distal end.

In use, the respiratory mask 310 is placed over the nose and mouth of a patient. FIG. 4b includes a schematic illustration of the flow of oxygen that is thought to occur when oxygen is introduced through the oxygen inlet 350 during use. In particular, FIG. 4b illustrates the flow of the oxygen introduced through the oxygen inlet 350 into the gases passageway 330 of the respiratory mask 310, from entry as a jet 360 to eventual exit through the open end of the gases passageway 330. In particular, when a supply of oxygen is connected to the gas inlet 350, a jet of gas is formed that follows a generally helical path (as described above in relation to the endotracheal tubes and the tracheotomy tube according to the invention). Also, as described above, this flow will become turbulent at a distal end of the gases passageway 330, thereby causing mixing of the oxygen with other gases in the gases passageway 330.

It has been found that this turbulent mixing of the oxygen with the other gases in the gases passageway 330 may provide Positive End Expiratory Pressure (PEEP) and/or Continuous Positive Airway Pressure (CPAP). This PEEP/CPAP may be relatively low, but may be adapted to be sufficient to keep the lungs of the patient at least partially inflated, and also increase the efficiency of gas exchange.

PEEP/CPAP is generated when the flow rate through the gas inlet 350 is sufficiently high, for a given size of exit orifice 352. This means that this respiratory mask 310 will provide PEEP/CPAP when the flow rate through the gas inlet 350 is above a threshold rate. In particular, this respiratory mask 310 has an exit orifice 352 of approximately 0.8 mm diameter, and it has been found that PEEP/CPAP is provided when the flow rate is approximately 15 litres per minute and above. Hence, where PEEP/CPAP is not required, the flow rate may be reduced to approximately 10 litres per minute, for example.

Figure 5:
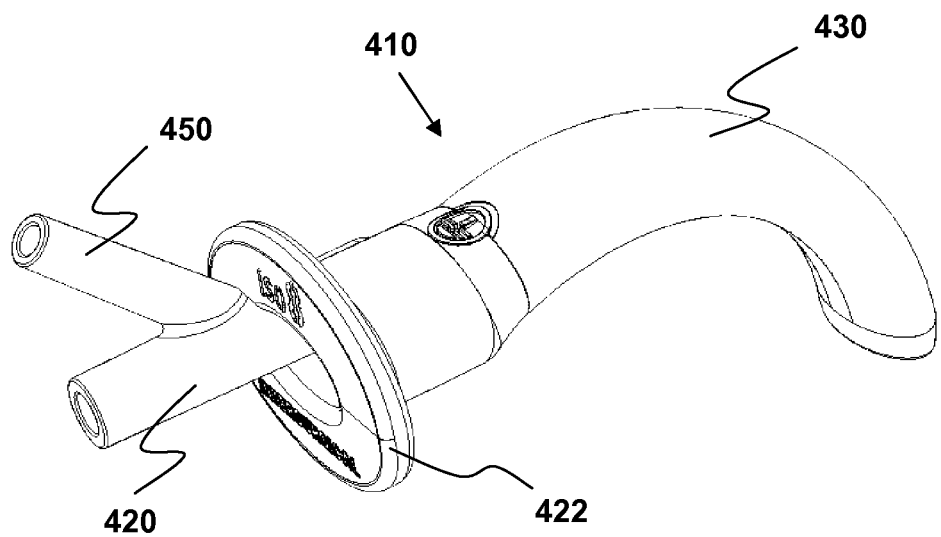
Figure 5:
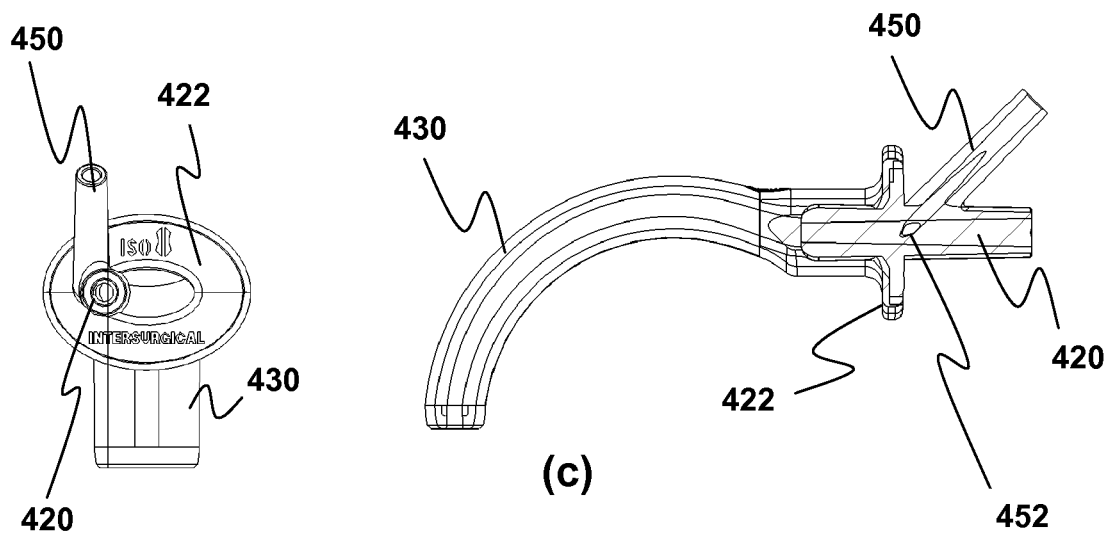

FIG. 5 shows three different views ((a), (b) and (c)) of a Guedel airway according to the invention, which is generally designated 410. The Guedel airway comprises a curved gases passageway 430 of substantially elliptical cross-section, with a peripheral flange 422 formed at a proximal end. The gases passageway 430 is open at its proximal and distal ends, these ends being orientated generally perpendicularly relative to each other. In addition, a proximal end portion of the Guedel airway 410 is formed with a greater wall thickness, which portion is adapted to be located between the patient's teeth, in use.

In contrast to a conventional Guedel airway, an auxiliary gases passageway 420 is provided within the proximal end portion of the Guedel airway 410. In particular, the auxiliary gases passageway 420 is tubular in form, with a circular cross-section, and projects from the proximal end of the Guedel airway 410 at one end, and terminates within the proximal end portion of the main gases passageway 430 of the Guedel airway 310 at the other end. A side wall of the auxiliary gases passageway 420 is bonded to an interior surface of the proximal end portion of the main gases passageway 430 at an apex of the oval shape, and the auxiliary gases passageway 420 extends parallel to the main gases passageway 430.

The auxiliary gases passageway 420 also includes an oxygen inlet 450 in the form of a generally cylindrical tube, which projects from the wall of the auxiliary gases passageway 420 in a similar manner to the manner in which oxygen inlets 50,150,250,350 project from the walls of the connectors 20,120,220 or gases passageway 330 in the endotracheal tubes 10,110, the tracheotomy tube 210 and the respiratory mask 310 described above. In particular, the oxygen inlet 450 is adapted to direct a jet of oxygen through an exit orifice 452, into the auxiliary gases passageway 420. The jet of oxygen is directed circumferentially along the internal surface of the auxiliary gases passageway 420, but also at an angle of approximately 45° to the principal direction of flow through the auxiliary gases passageway 420, thereby causing the jet of oxygen to follow a helical path along the auxiliary gases passageway 420 towards the end located within the proximal end portion of the main gases passageway 430 of the Guedel airway 410.

In use, the Guedel airway 410 is inserted into a patient's mouth with the end of the distal end of the gases passageway 430 entering first. The Guedel airway 410 is inserted in an inverted orientation so that, once inserted a certain distance, the gases passageway 430 curves towards the upper surface of the patient's upper airway. The Guedel airway 410 is then rotated through 180° and inserted further into the patient's mouth so that the gases passageway 430 curves downwards into the oropharynx. The Guedel airway 10 is positioned so that the patient's teeth rest on the exterior of the proximal end portion of the gases passageway 430 and the flange 422 is located externally of the patient's teeth. The flange 422 prevents the Guedel airway 410 from slipping further into the patient's airway.

When a supply of oxygen is connected to the oxygen inlet 450, a jet of gas is formed that follows a generally helical path (as described above in relation to the endotracheal tubes, the tracheotomy tube and the respiratory mask) along the auxiliary gases passageway 420. This flow will become turbulent at a distal end of the auxiliary gases passageway 420 (within the proximal end portion of the main gases passageway 430), thereby causing mixing of the oxygen with other gases in the auxiliary gases passageway 420.

It has been found that this turbulent mixing of the oxygen with the other gases in the auxiliary gases passageway 420 may provide Positive End Expiratory Pressure (PEEP) and/ or Continuous Positive Airway Pressure (CPAP). This PEEP/CPAP may be relatively low, but may be adapted to be sufficient to keep the lungs of the patient at least partially inflated, and also increase the efficiency of gas exchange.

PEEP/CPAP is generated when the flow rate through the gas inlet 450 is sufficiently high, for a given size of exit orifice 452. This means that this Guedel airway 410 will provide PEEP/CPAP when the flow rate through the gas inlet 450 is above a threshold rate. In particular, this Guedel airway 410 has an exit orifice 452 of approximately 0.8 mm diameter, and it has been found that PEEP/CPAP is provided when the flow rate is approximately 15 litres per minute and above. Hence, where PEEP/CPAP is not required, the flow rate may be reduced to approximately 10 litres per minute, for example.

Figure 6A:
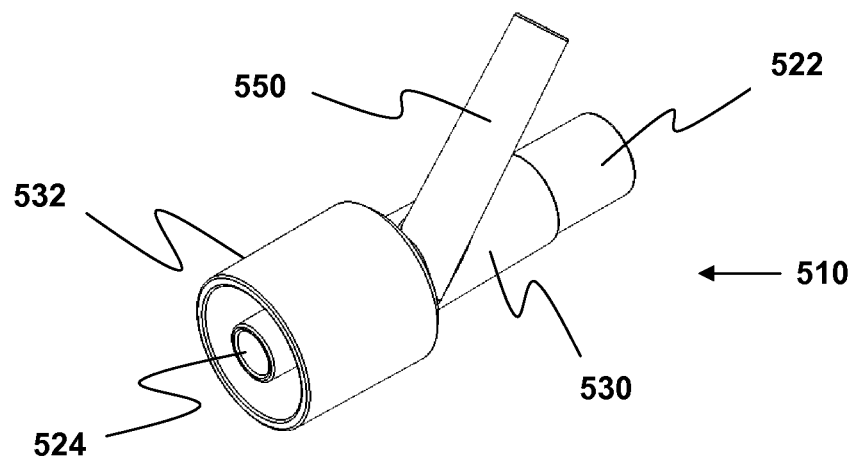
FIG. 6a is a perspective view of an oxygenating device according to the invention.
Figure 6B:
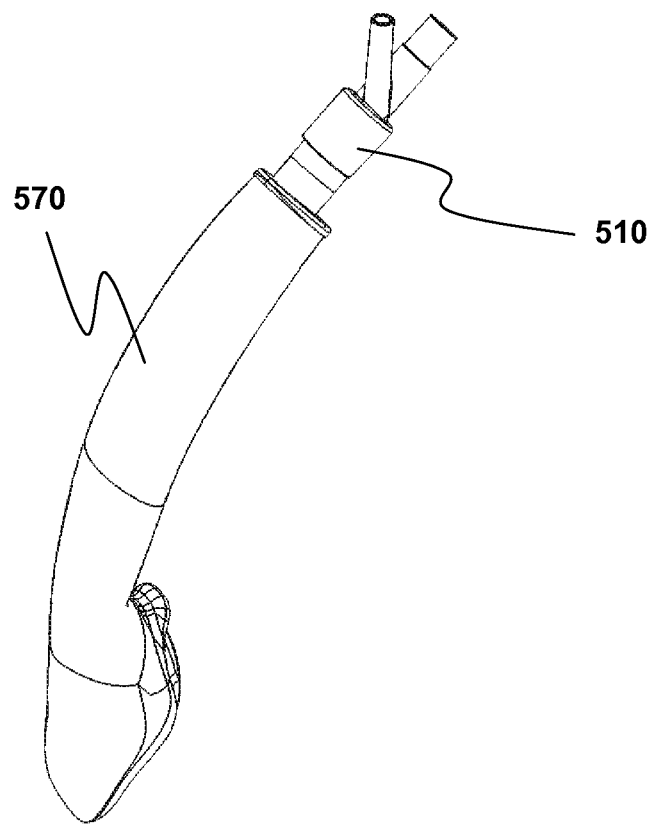
FIG. 6b is a perspective view of the oxygenating device of FIG. 6a, connected to a supraglottic airway.
Figure 6C:
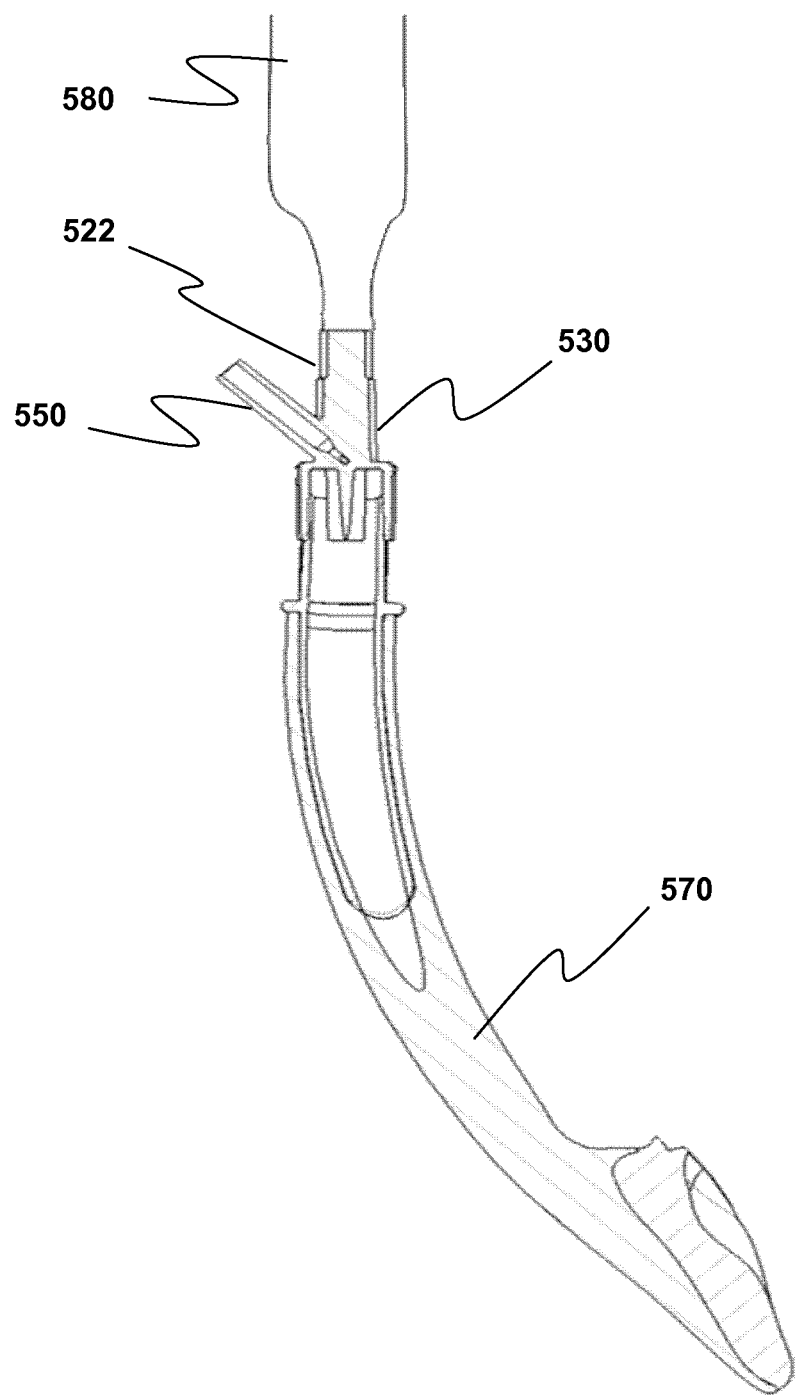
FIG. 6c is a cross-sectional view of the oxygenating device of FIG. 6a, connected to both a supraglottic airway and a bag.

FIGS. 6a to 6c show an oxygenating device according to the invention, which is generally designated 510. As can be seen in FIG. 6a, the oxygenating device 510 has a gases passageway 530 of circular cross-section. A proximal end of the gases passageway 530, which is designated 522, is open to the atmosphere. A distal end of the gases passageway 530 has an open end, and a co-axial skirt adapted to engage the inlet to an airway device, such as a supraglottic airway 570 (see FIGS. 6b and 6c), such that the gases passageway 530 of the oxygenating device 510 is in sealed fluid communication with the airway device. In addition, as shown in FIG. 6c, the distal end of the gases passageway 522 can connect to a bag 580 with an exhalation opening, or even simply strips of material such as plastic or cloth, such that exhaled gases from the patient cause the bag 580 or strips of material to move, thus providing a visible and/or audible indication that the patient is breathing.

The oxygenating device 510 also includes an oxygen inlet 550, which has a similar arrangement to the oxygen inlets 50,150,250,350,450 of the respiratory devices 10,110,210, 310,410 described above. In particular, the oxygen inlet 550 is adapted to direct a jet of oxygen into the gases passageway 530 of the oxygenating device 510. The jet of oxygen is directed circumferentially along the internal surface of the gases passageway 530, but also at an angle of approximately 45° to the principal direction of flow through the gases passageway 530 of the oxygenating device 510, thereby causing the jet of oxygen to follow a helical path along the gases passageway 530 towards the distal end. Furthermore, the jet of oxygen thereafter follows a helical path along the interior surface of the gases passageway of the connected airway device, e.g. the supraglottic airway 570, towards the distal end of that device 570.

The arrangement of the oxygen inlet 550 causes oxygen to be introduced into the gases passageway of the connected airway device, e.g. the supraglottic airway 570, in a manner that provides substantial advantages over the prior art. In particular, it has been found that oxygen introduced through the oxygen inlet 550 mixes with the other gases in the gases passageway of the connected airway device, e.g. the supraglottic airway 570, further along the gases passageway, and in particular closer to the distal end of the gases passageway, than in prior art arrangements.

In addition, the helical flow of oxygen will become turbulent at a distal end of the gases passageway of the airway device, e.g. the supraglottic airway 570, thereby causing mixing of the oxygen with other gases in the gases passageway. It has been found that this turbulent mixing of the oxygen with the other gases in the gases passageway may provide Positive End Expiratory Pressure (PEEP) and/ or Continuous Positive Airway Pressure (CPAP). This PEEP/CPAP may be relatively low, but may be adapted to be sufficient to keep the lungs of the patient at least partially inflated, and also increase the efficiency of gas exchange.

PEEP/CPAP is generated when the flow rate through the gas inlet 550 is sufficiently high, for a given size of exit orifice. This means that this oxygenating device 510 will provide PEEP/CPAP when the flow rate through the gas inlet 550 is above a threshold rate. In particular, this oxygenating device 510 has an exit orifice of approximately 0.8 mm diameter, and it has been found that PEEP/CPAP is provided when the flow rate is approximately 15 litres per minute and above. Hence, where PEEP/CPAP is not required, the flow rate may be reduced to approximately 10 litres per minute, for example.

Figure 7:
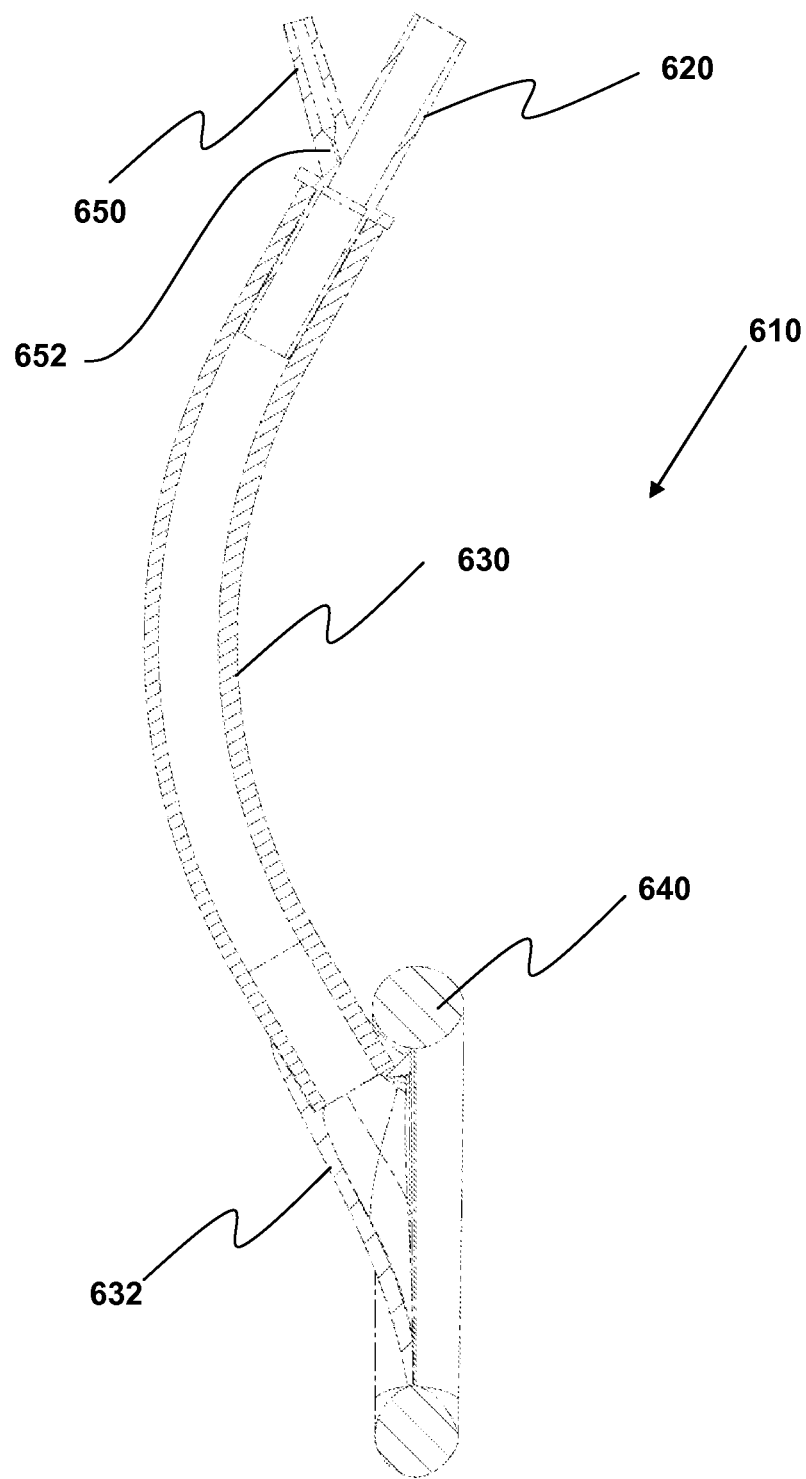
FIG. 7 is a cross-sectional view of a laryngeal mask airway according to the invention.

FIG. 7 shows a laryngeal mask airway according to the invention, which is generally designated 610. The laryngeal mask airway 610 comprises a connection component 620, a gases passageway 630 and an inflatable cuff 640. The laryngeal mask airway 610 is adapted to be inserted into the airway of a patient, through the mouth, such that the connection component 220 projects from the patient's mouth, and the inflatable cuff 640 is accommodated within the laryngeal inlet region of the patient.

The gases passageway 630 is a generally flexible tube of substantially constant circular cross-section, which is engaged with the connection component 620 at its proximal end and is connected to the inflatable cuff 640 at its distal end by a flared connecting web 632.

The inflatable cuff 640 at one end of the gases passageway 630 is generally elliptical in shape, and is adapted to form a seal with the laryngeal inlet of the patient, in use. The inflatable cuff 640 defines an entrance to the laryngeal mask airway 610, such that the laryngeal inlet of the patient is in fluid communication with the gases passageway 630 of the laryngeal mask airway 610 through the flared web 632.

The connection component 620 at the other end of the gases passageway 630 has the same form as the connection component 20 of the endotracheal tube 10 of FIG. 1, which is described above, and has a similarly arranged oxygen inlet 650. In particular, the oxygen inlet 650 is adapted to direct a jet of oxygen through an exit orifice 652, into the gases passageway 630. The jet of oxygen is directed circumferentially along the internal surface of the gases passageway 630, but also at an angle of approximately 45° to the principal direction of flow through the gases passageway 630, thereby causing the jet of oxygen to follow a helical path along the gases passageway 630 towards the distal end.

The arrangement of the oxygen inlet 650 causes oxygen to be introduced into the gases passageway 630 of the laryngeal mask airway 610 in a manner that provides substantial advantages over the prior art. In particular, it has been found that the oxygen introduced through the oxygen inlet 650 mixes with the other gases in the gases passageway 630 of the laryngeal mask airway 610 further along the gases passageway 630, and in particular closer to the distal end of the gases passageway 630, than in prior art arrangements.

In addition, the helical flow of oxygen will become turbulent at a distal end of the gases passageway 630 of the laryngeal mask airway 610, thereby causing mixing of the oxygen with other gases in the gases passageway 630. It has been found that this turbulent mixing of the oxygen with the other gases in the gases passageway may provide Positive End Expiratory Pressure (PEEP) and/or Continuous Positive Airway Pressure (CPAP). This PEEP/CPAP may be relatively low, but may be adapted to be sufficient to keep the lungs of the patient at least partially inflated, and also increase the efficiency of gas exchange.

PEEP/CPAP is generated when the flow rate through the gas inlet 650 is sufficiently high, for a given size of exit orifice 652. This means that this laryngeal mask airway 610 will provide PEEP/CPAP when the flow rate through the gas inlet 650 is above a threshold rate. In particular, this laryngeal mask airway 610 has an exit orifice 652 of approximately 0.8 mm diameter, and it has been found that PEEP/CPAP is provided when the flow rate is approximately 15 litres per minute and above. Hence, where PEEP/CPAP is not required, the flow rate may be reduced to approximately 10 litres per minute, for example.

Figure 8:
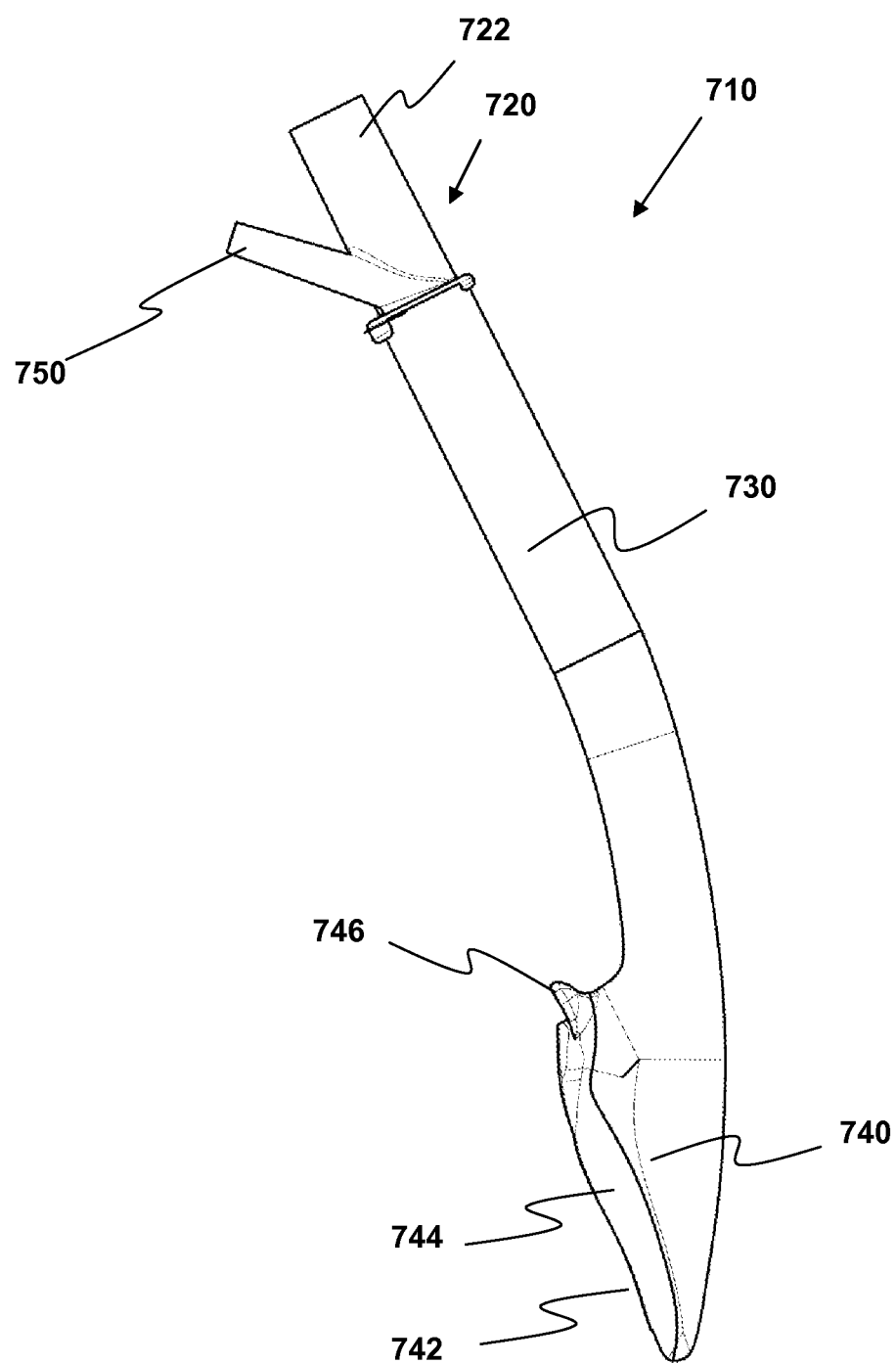
FIG. 8 is a side view of a supraglottic airway device according to the invention.
Figure 9:
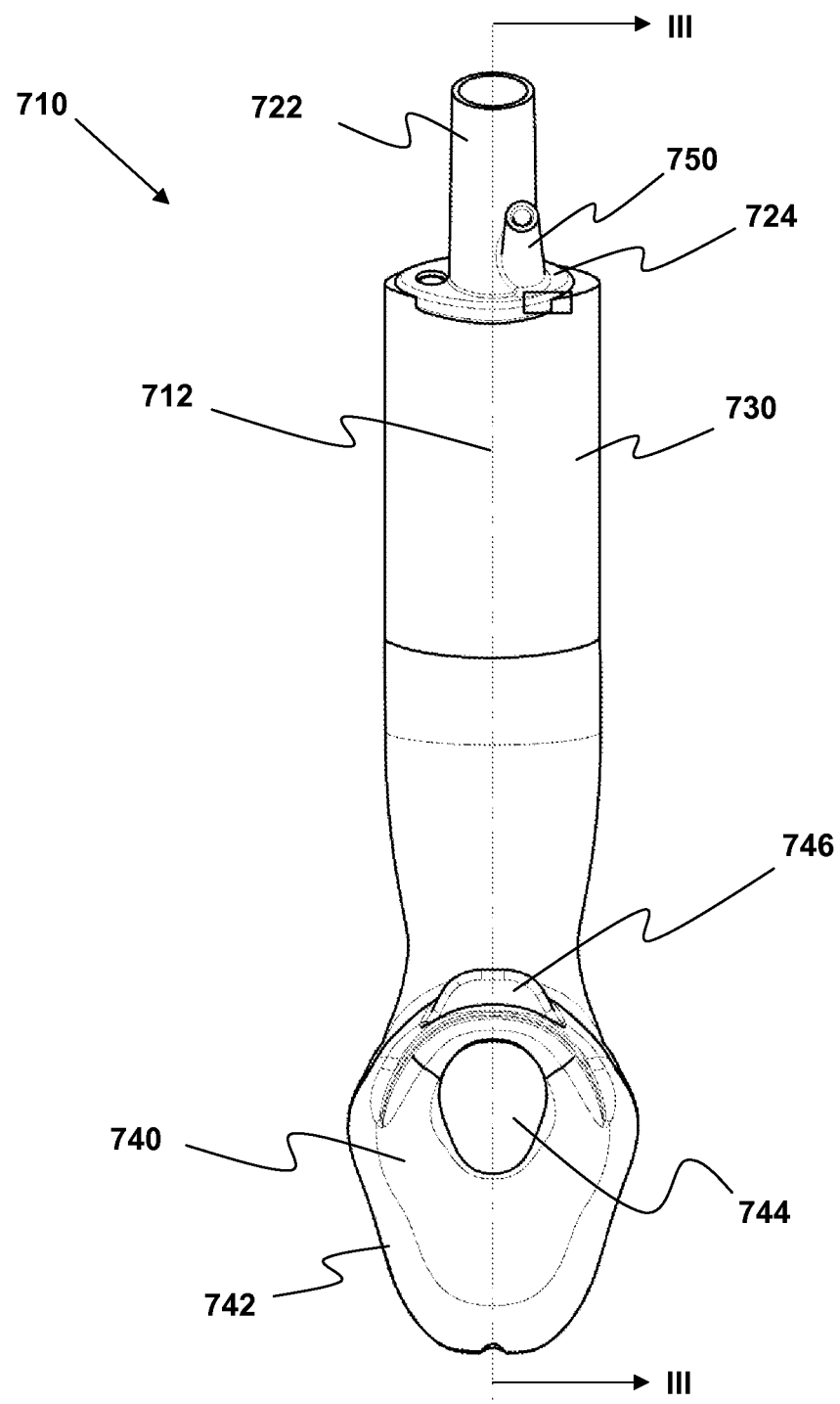
FIG. 9 is a front view of the supraglottic airway device of FIG. 8.
Figure 10:
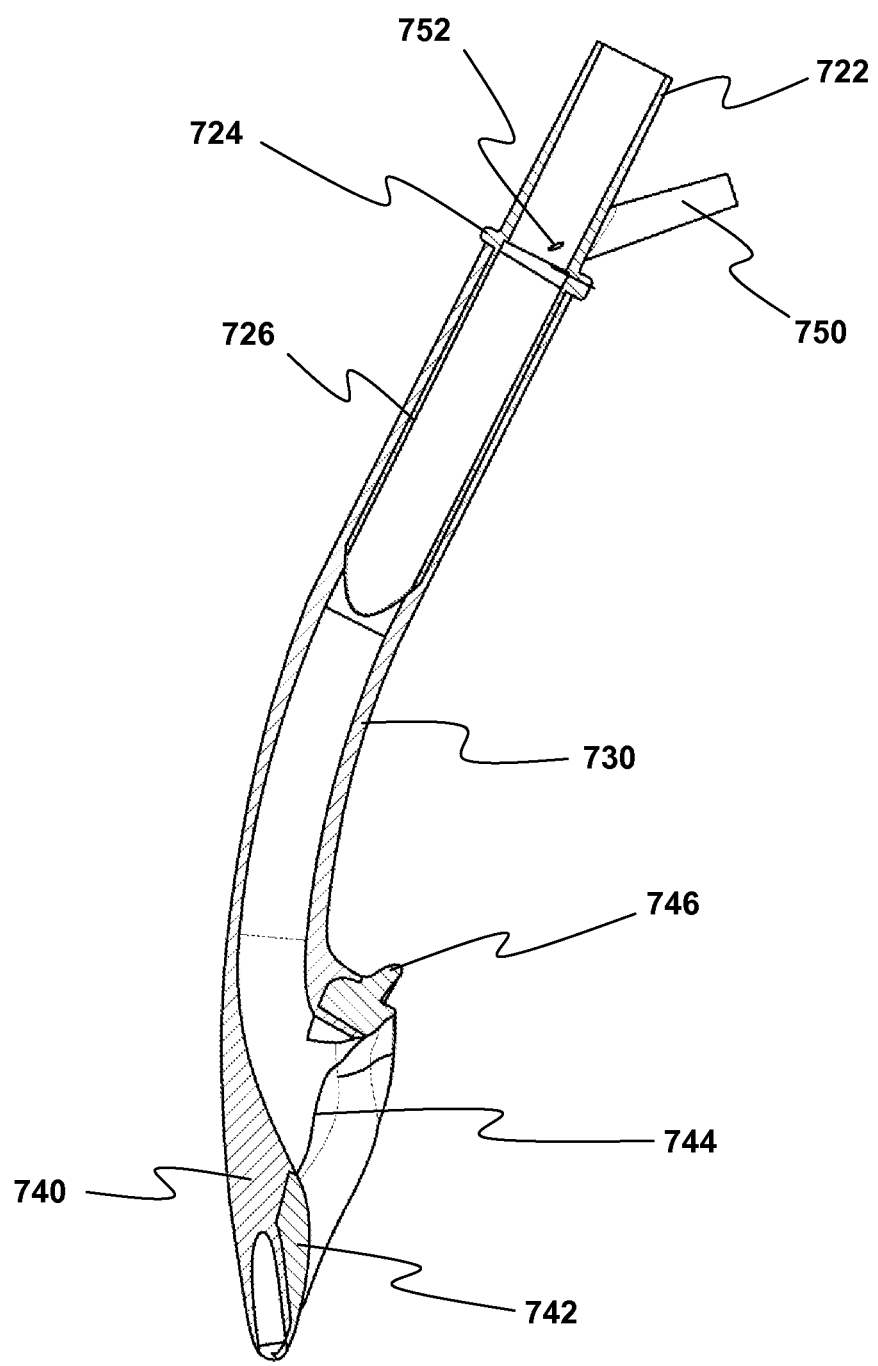
FIG. 10 is a cross-sectional view of the supraglottic airway device along the line III-III in FIG. 9.

FIGS. 8 to 10 show a supraglottic airway device according to the invention, which is generally designated 710. The supraglottic airway device 710 comprises a connection component 720, an airway tube 730 and a cuff 740. The supraglottic airway device 710 is adapted to be inserted into the airways of a patient, through the mouth, such that the connection component 720 projects from the patient's mouth, and the cuff 740 is accommodated within the laryngeal inlet region of the patient.

The airway tube 730 is a generally flexible tube, which defines a gases passageway of substantially constant circular cross-section, which is engaged with the connection component 720 at its proximal end and is integrally formed with the cuff 740 at its distal end. The internal and external diameters of the airway tube 730 are chosen to correspond to the size of the patient, e.g. adult or pediatric, and also to accommodate associated ancillary devices, such as endotracheal tubes.

The connection component 720 comprises a male tubular connector 722 suitable for connection to a conventional breathing circuit, and a co-axial engagement member 726 that is received within the proximal end of the airway tube 730 with a close fit. The connector 722 and the engagement member 726 together define a gases passageway of substantially constant circular cross-section. The airway tube 730 includes a circumferential recess on its interior surface, at its proximal end, which is adapted to receive the engagement member 726, such that there is a smooth transition between the interior surfaces of the connection component 720 and the airway tube 730. In addition, an outwardly projecting support flange 724 is provided between the connector 722 and the engagement member 726, which abuts the end of the airway tube 730.

The cuff 740 is sized and shaped to correspond to the laryngeal inlet region of a patient, and is adapted to cover and form a seal with the laryngeal inlet of the patient, in use. The cuff 740 comprises a sealing member 742 that defines a front face of the cuff 740, and extends about an opening 744 in the cuff 740. The sealing member 742 is adapted to provide an effective seal around the laryngeal inlet of the patient, in use, and also includes an epiglottic rest 746 located at the proximal end of the cuff 740. This epiglottic rest 746 is sized and shaped so as to be anatomically positioned against the epiglottis, to ensure a proper seal with the laryngeal inlet of the patient, and to prevent the epiglottis from folding down towards the laryngeal inlet, in use, which may cause an obstruction to airflow.

The cuff 740 also includes a gases passageway, which extends from the airway tube 730 at a proximal end of the cuff 740, to the opening 744 at a distal end of the cuff 740. The gases passageways of the connection component 720, the airway tube 730, and the opening 744 of the cuff 740, therefore enable fluid communication between the connector 722 at one end of the supraglottic airway device 710, and the opening 744 of the cuff 740 at the other end of the supraglottic airway device 710.

The connection component 720 is formed of a substantially rigid material, such as polypropylene, such that a patient may bite the connection component 720 without it collapsing, during use. The airway tube 730 and the cuff 740, however, are integrally formed of a material that is softer and more deformable, in order to reduce the risk of trauma to the patient, but still sufficiently rigid to prevent collapse of the airway tube 730 and cuff 740 during use. In particular, in this embodiment, the airway tube 730 and cuff 740 are integrally formed of Styrene Ethylene Butylene Styrene (SEBS) including white paraffin oil as a plasticising agent. The sealing member 742 of the cuff 740 is also formed of SEBS, but has a greater concentration of plasticising agent, relative to the remainder of the cuff 740 and airway tube 730. The sealing member 742 is therefore more deformable than the remainder of the cuff 740, in order to improve its sealing properties.

The supraglottic airway device 710 shown in FIGS. 8 to 10 generally corresponds in form to the supraglottic airway device described in WO 2005/016427 A2. However, the supraglottic airway device 710 shown in FIGS. 8 to 10 includes an oxygen inlet 750, as part of the connection component 720, which is not disclosed by WO 2005/016427 A2. This oxygen inlet 50 has a similar arrangement to the oxygen inlets 50,150,250,350,450,550,650 described above in relation to the other respiratory devices 10,110,210,310, 410,510,610 that are specifically described.

In particular, the oxygen inlet 750 has the form of a generally cylindrical tube, which projects from the connection component 720, and is adapted for connection to a supply of oxygen. In particular, the oxygen inlet 750 projects from the wall of the connector 720, from a position adjacent to the support flange 724, and offset from a medial plane of the device (designated 712 in FIG. 2). The oxygen inlet 750 extends at an angle of approximately 45° to the connector 722, in the direction of the proximal end of the connector 722.

Figure 11:
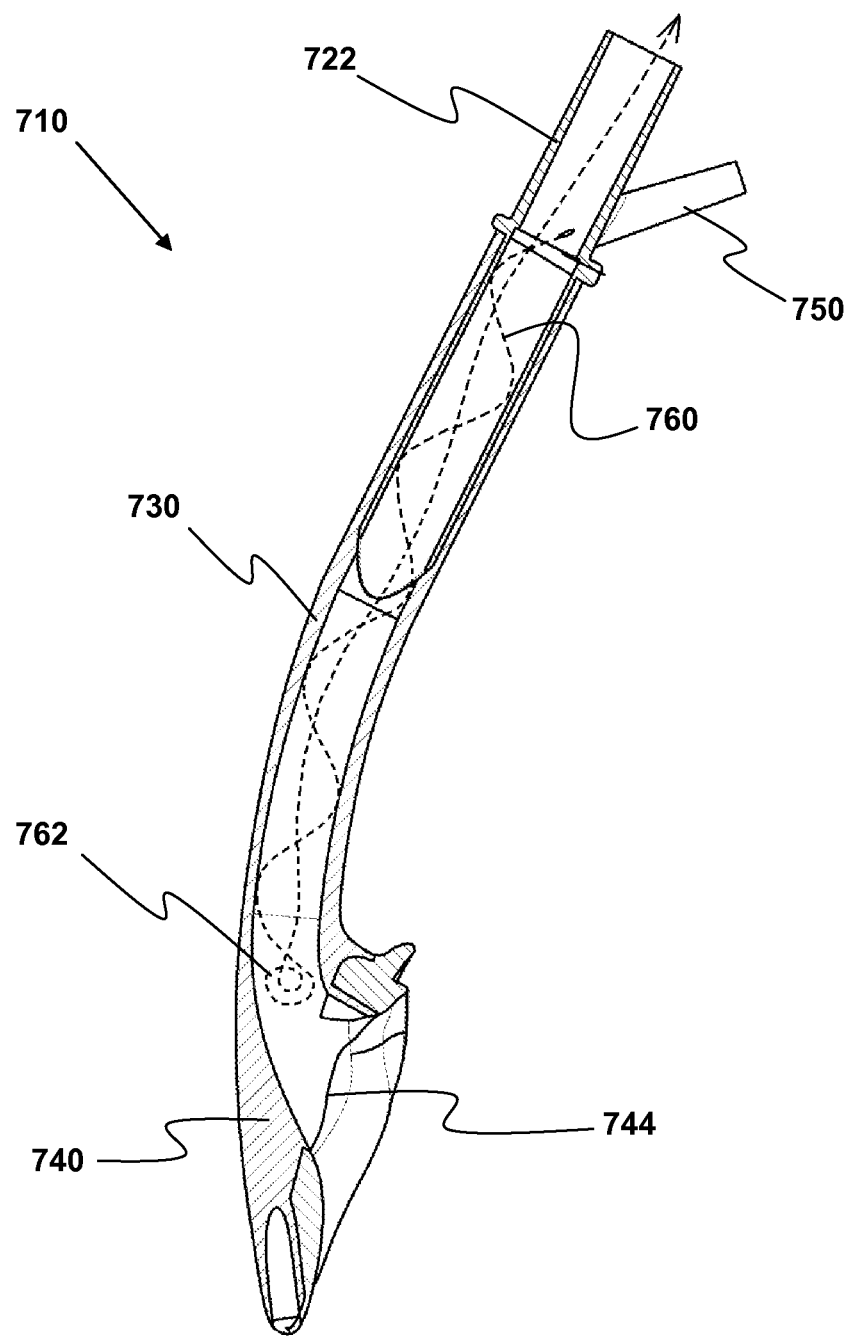
FIG. 11 is a cross-sectional view of the supraglottic airway device along the line III-III in FIG. 9, which includes a schematic illustration of airflow within the device during use.
Figure 12:
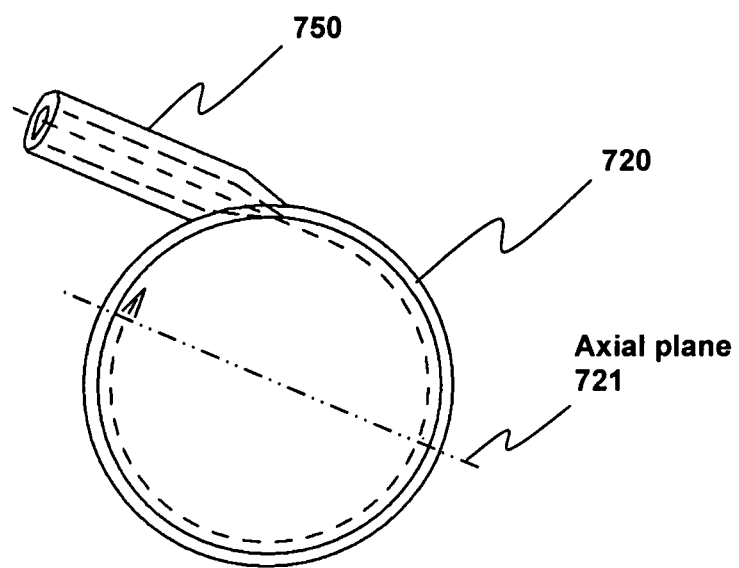
FIG. 12 is a schematic illustration of the orientation of an oxygen inlet and a gases passageway for the supraglottic airway device of FIGS. 8-11.

The interior of the oxygen inlet 750 forms a gases passageway with a substantially constant cross-section, but which reduces in diameter as it approaches the wall of the connector 722 and terminates at a small exit orifice 752 (see FIGS. 10-12). In particular, the exit orifice 752 has a diameter of approximately 0.8 mm, which has been found to be effective for a gases passageway through the device of approximately 15 mm diameter. The oxygen inlet 750 has a slightly tapered exterior that facilitates connection to the supply of oxygen.

The oxygen inlet 750 is adapted to direct a jet of oxygen through the exit orifice 752, into the gases passageway of the device 710. The jet of oxygen is directed circumferentially along the internal surface of the connection component 720, as shown in FIG. 12, but also at an angle of approximately 45° to the principal direction of flow through the gases passageway of the device 710, thereby causing the jet of oxygen to follow a helical path along the gases passageway towards the distal end.

The orientation of the oxygen inlet 750 and the size of the exit orifice 752 cause oxygen to be introduced into the gases passageway of the device 710 in a manner that provides substantial advantages over the prior art. In particular, it has been found that the oxygen introduced through the oxygen inlet 750 mixes with the other gases in the gases passageway of the device further along the gases passageway, and in particular closer to the distal end of the gases passageway, than in prior art arrangements.

It is presently thought that the flow of oxygen, in use, in the supraglottic airway device 710 occurs along the lines of that schematically illustrated in FIG. 11. In particular, FIG. 11 shows a schematic illustration of the flow of the oxygen introduced through the oxygen inlet 750 into the gases passageway of the device 710, from entry as a jet 760 through the exit orifice 752 to eventual exit through the connector 722 of the device 710. In particular, a jet of oxygen 760 is directed by the oxygen inlet 750 along the interior surface of the device 10, at an angle of approximately 45° to the principal directions of flow through the gases passageway. The jet of oxygen 760 initially has a linear path, but a centripetal force is imparted by the interior surface of the device 710, which causes the jet of oxygen 760 to travel along a generally helical path. It is thought that the combination of the momentum of the jet of oxygen 760 introduced through the gas inlet 750, and the centripetal force applied by the interior surface of the device 710, acts to maintain the helical flow of oxygen in a radially outer region of the gases passageway.

As the jet of oxygen 760 travels along the gases passageway of the device 710, it gradually loses momentum until its momentum is no longer sufficient to maintain the helical flow of oxygen in a radially outer region of the gases passageway. The flow of oxygen will then become turbulent in a radially inner region of the gases passageway, thereby causing mixing of the oxygen with the other gases in the gases passageway. This region of turbulent flow 762 is shown in FIG. 11 as occurring adjacent the cuff 740 of the device 710, near to the opening 744 and hence the laryngeal inlet of the patient.

The present invention therefore enables an oxygen inlet 750 to be provided at a proximal end of an supraglottic airway device 710, e.g. externally of a patient, such that the oxygen introduced into the supraglottic airway device 710 only mixes with the other gases to be inhaled by the patient at a distal end of the supraglottic airway device 710, e.g. near the laryngeal inlet of the patient. This invention therefore increases the concentration of oxygen that is inhaled by a patient relative to arrangements in which oxygen is supplied at the proximal end of a supraglottic airway device, and mixes with the other gases in the gases passageway of the device at that end.

It has also been found that where high flow rates of oxygen are supplied to the gas inlet 750, the turbulent flow generated when the gas mixes with the other gases in the gases passageway provides a resistance to exhalation of the patient, and may therefore provide Positive End Expiratory Pressure (PEEP) and/or Continuous Positive Airway Pressure (CPAP). This PEEP/CPAP may be relatively low, but may be adapted to be sufficient to keep the lungs of the patient at least partially inflated, and also increase the efficiency of gas exchange.

PEEP/CPAP is generated when the flow rate through the gas inlet 750 is sufficiently high, for a given size of exit orifice 752. This means that this supraglottic airway device 710 will provide PEEP/CPAP when the flow rate through the gas inlet 750 is above a threshold rate. In particular, this supraglottic airway device 710 has an exit orifice 752 of approximately 0.8 mm diameter, and it has been found that PEEP/CPAP is provided when the flow rate is approximately 15 litres per minute and above. Hence, where PEEP/CPAP is not required, the flow rate may be reduced to approximately 10 litres per minute, for example.

In addition, since the supraglottic airway device 710 may be used to provide a turbulent region of oxygen, at a relatively high concentration, and in a distal region of the gases passageway, the supraglottic airway device 710 is also particularly advantageous for use in passive oxygenation. In particular, where a patient is not breathing, a supply of oxygen may be connected to the gas inlet 750 of the supraglottic airway device 710, with the connector 722 being open to the atmosphere. It has been found that a turbulent flow of oxygen in a distal region of the gases passageway, as provided by this arrangement of the supraglottic airway device 710, may promote gas exchange between the supraglottic airway device 710 and the lungs of the patient more effectively than simple Brownian gas diffusion. This may be particularly advantageous in resuscitation.

Figure 13:
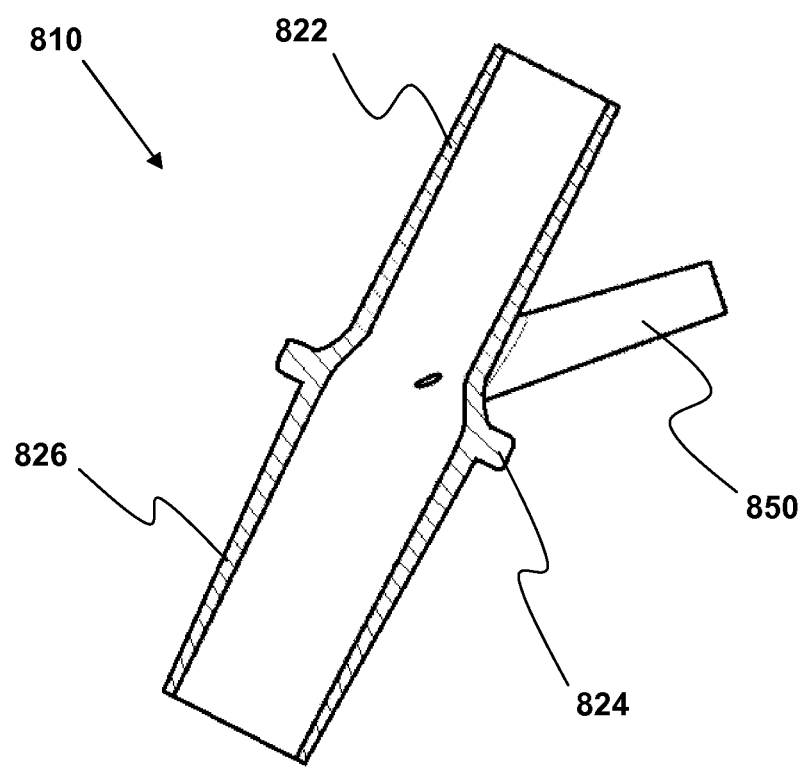
FIG. 13 is a cross-sectional view of an adaptor according to the invention.

Finally, FIG. 13 shows an adaptor according to the invention, which is generally designated 810. The adaptor 810 comprises a male tubular connector 822 and a female tubular connector 826, which together define a gases passageway through the adaptor 810. In addition, an outwardly projecting support flange 824 is provided between the connectors 822,826.

The adaptor 810 includes an oxygen inlet 850 which is identical to the oxygen inlets of the respiratory devices described above, and is similarly configured relative to the connector 822 from which the oxygen inlet 850 projects.

The adaptor 810 is adapted to engage a conventional respiratory device, such as a laryngeal mask airway, and provide an oxygen inlet 850 as described above in relation to the respiratory devices according to the invention. In particular, the female tubular connector 826 is adapted to receive a corresponding male connector of a conventional respiratory device, such that the jet of oxygen provided by the oxygen inlet 850 is directed along the interior surface of the gases passageway of the otherwise conventional respiratory device. The jet of oxygen will then flow along the gases passageway of the connected respiratory device in the same manner as that described above in relation to the other specific embodiments of the invention, provided that the interior surface of the gases passageway of the respiratory device is sufficiently smooth to maintain the helical flow.

The adaptor 810 may therefore be connected to the proximal end of a conventional respiratory device, and provide the advantages of the present invention as described above.

The invention claimed is:

1. A respiratory device for delivering gas to a patient, the device comprising:
    a gases passageway having a proximal end, configured to receive a principal flow of gases, a distal end, and a first longitudinal axis;
    a supplementary gas inlet positioned in a non-rotatable fixed orientation directly in a side wall of a portion of the gases passageway, wherein the supplementary gas inlet comprises a longitudinal member having a proximal end adapted to be connected to a supply of gas, a distal end in fluid communication with an exit orifice in the side wall of the gases passageway, and a second longitudinal axis that extends in a direction that does not intersect the first longitudinal axis of the gases passageway but intersects a plane extending through the first longitudinal axis at an oblique angle, whereby the exit orifice is positioned in the side wall such that the supplementary gas inlet, in use, directs a jet of gas through said exit orifice in the side wall of the gases passageway circumferentially along an interior surface of the gases passageway in order to generate helical flow along the interior surface of the gases passageway, such that the jet of gas follows a generally helical path towards the distal end of the gases passageway, wherein the helical flow along the interior surface of the gases passageway prevents mixing of the jet of gas with the principal flow of gases adjacent the exit orifice, but toward the distal end of the gases passageway, as momentum of the jet of gas decreases, the jet of gas mixes with the principal flow of gases in the gases passageway.

2. A respiratory device as claimed in claim 1, wherein the exit orifice has an area that is smaller than an area defined by the proximal end of the supplementary gas inlet.

3. A respiratory device as claimed in claim 1, wherein the supplementary gas inlet projects from the side wall of the gases passageway, in a direction that is parallel to, but offset from, an axial plane extending through the first longitudinal axis of the portion of the gases passageway in which the supplementary gas inlet is formed.

4. A respiratory device as claimed in claim 1, wherein the supplementary gas inlet projects from the gases passageway at an angle to the portion of the gases passageway in which the supplementary gas inlet is formed, in a direction towards the proximal end of the gases passageway.

5. A respiratory device as claimed in claim 1, wherein the exit orifice has an area that is smaller than an internal cross-sectional area of the gases passageway.

6. A respiratory device as claimed in claim 1, wherein the supplementary gas inlet extends from the side wall of the gases passageway at an oblique angle to a longitudinal axis of the gases passageway to direct the jet of gas introduced into the supplementary gas inlet into the off-axis portion of the gases passageway.

7. A respiratory device as claimed in claim 1, wherein no ancillary devices or conduits are provided in the gases passageway, such that the passageway is unobstructed.

8. A respiratory device as claimed in claim 1, wherein the momentum of the gas directed along the interior surface of the gases passageway by the supplementary gas inlet, and the centripetal force applied by the interior surface of the gases passageway, act to maintain the flow of the gas in a radially outer region of the gases passageway, until the momentum of the gas reduces sufficiently for the gas flow to become turbulent in a radially inner region of the gases passageway, thereby causing mixing of the gas with the other gases in the gases passageway.

9. A method of delivering gas to a patient, which method comprises the steps of:
    (a) providing a respiratory device for delivering gas to a patient, the device comprising a gases passageway having a proximal end, configured to receive a principal flow of gases, a distal end, and a first longitudinal axis;
    (b) directing a jet of gas, through a supplementary gas inlet positioned in a non-rotatable fixed orientation directly in a side wall of a portion of the gases passageway and comprising a longitudinal member having a proximal end adapted to be connected to a supply of gas, a distal end in fluid communication with an exit orifice in the side wall of the gases passageway, and a second longitudinal axis that extends in a direction that does not intersect the first longitudinal axis of the gases passageway but intersects a plane extending through the first longitudinal axis at an oblique angle, whereby the exit orifice is positioned in the side wall such that supplementary gas inlet directs the jet of gas through said exit orifice in the side wall of the gases passageway circumferentially along an interior surface of the gases passageway in order to generate helical flow along the interior surface of the gases passageway, such that the jet of gas follows a generally helical path towards the distal end of the gases passageway, wherein the helical flow along the interior surface of the gases passageway prevents mixing of the jet of gas with the principal flow of gases adjacent to the exit orifice, but toward the distal end of the gases passageway, as momentum of the jet of gas decreases, the jet of gas mixes with the principal flow of gases in the gases passageway.

10. A method as claimed in claim 9, wherein the gas is introduced at a proximal region of the gases passageway, and the gas mixes with other gases in the gases passageway when it reaches a distal region of the gases passageway.

11. A method as claimed in claim 9, wherein the flow of gas is maintained in a radially outer region of the gases passageway until the momentum of the gas reduces sufficiently for the gas flow to become turbulent in a radially inner region of the gases passageway, thereby causing mixing of the gas with the other gases in the gases passageway.

12. A method as claimed in claim 9, wherein the gas directed along an interior surface of the gases passageway is mixed with gases that are supplied through the proximal end of the gases passageway, either from a respiratory apparatus to which the device is connected or from the atmosphere, and the gases that are exhaled by the patient.

13. A method as claimed in claim 9, wherein gas directed along an interior surface of the gases passageway, such that the gas follows a generally helical path towards the distal end of the gases passageway, is oxygen.

14. A method as claimed in claim 9, wherein the jet of gas directed through the supplementary gas inlet consists of gas.

15. An adaptor for use with a respiratory device for delivering gas to a patient, the adaptor comprising:
   a gases passageway having a proximal end, configured to receive a principal flow of gases, a distal end adapted for connection to a proximal end of the gases passageway of the respiratory device, and a first longitudinal axis;
   a supplementary gas inlet positioned in a non-rotatable fixed orientation directly in a side wall of a portion of the gases passageway of the adaptor, wherein the supplementary gas inlet comprises longitudinal member having a proximal end adapted to be connected to a supply of gas, a distal end in fluid communication with an exit orifice in the side wall of the gases passageway, and a second longitudinal axis that extends in a direction that does not intersect the first longitudinal axis of the gases passageway but intersects a plane extending through the first longitudinal axis at an oblique angle, whereby the exit orifice is positioned in the side wall such that the supplementary gas inlet, in use, directs a jet of gas through said exit orifice in the side wall of the gases passageway circumferentially along an interior surface of the gases passageway in order to generate helical flow along the interior surface of the gases passageway of the adaptor and/or the respiratory device, such that the jet of gas follows a generally helical path towards a distal end of the gases passageway of the respiratory device, wherein the helical flow along the interior surface of the gases passageway prevents mixing of the jet of gas with the principal flow of gases adjacent the exit orifice, but toward the distal end of the gases passageway, as momentum of the jet of gas decreases, the jet of gas mixes with the principal flow of gases in the gases passageway.

16. An adaptor as claimed in claim 15, wherein the exit orifice has an area that is smaller than an area defined by the proximal end of the supplementary gas inlet.

17. An adaptor as claimed in claim 15, wherein the supplementary gas inlet projects from the side wall of the gases passageway, in a direction that is parallel to, but offset from, an axial plane extending through the first longitudinal axis of the portion of the gases passageway in which the supplementary gas inlet is formed.

18. An adaptor as claimed in claim 15, wherein the supplementary gas inlet projects from the gases passageway at an angle to the portion of the gases passageway in which the supplementary gas inlet is formed, in a direction towards the proximal end of the gases passageway.

19. An adaptor as claimed in claim 15, wherein the exit orifice has an area that is smaller than an internal cross-sectional area of the gases passageway.

20. An adaptor as claimed in claim 15, wherein the supplementary gas inlet extends from the side wall of the gases passageway at the oblique angle to the first longitudinal axis of the gases passageway to direct the jet of gas introduced into the supplementary gas inlet into the off-axis portion of the gases passageway.

21. An adapter as claimed in claim 15, wherein no ancillary devices or conduits are provided in the gases passageway, such that the passageway is unobstructed.

22. An adaptor as claimed in claim 15, wherein the momentum of the gas directed along the interior surface of the gases passageway by the supplementary gas inlet, and the centripetal force applied by the interior surface of the gases passageway, act to maintain the flow of the gas in a radially outer region of the gases passageway, until the momentum of the gas reduces sufficiently for the gas flow to become turbulent in a radially inner region of the gases passageway, thereby causing mixing of the gas with the other gases in the gases passageway.

23. A respiratory device for delivering gas to a patient, comprising:
   an adapter and an airway tube, the adapter comprising:
      a gases passageway having a proximal end comprising a male tubular connector, configured for connection to a conventional breathing circuit to receive a principal flow of gases, a distal end comprising a co-axial engagement member that is received within a proximal end of the airway tube with a close fit, and a first longitudinal axis;
      a supplementary gas inlet positioned in a non-rotatable fixed orientation directly in a side wall of a portion of the gases passageway, wherein the supplementary gas inlet comprises a longitudinal member having proximal end adapted to be connected to a supply consisting of gas, a distal end in fluid communication with an exit orifice in the side wall of the gases passageway, and a second longitudinal axis that extends in a direction that does not intersect the first longitudinal axis of gases passageway but intersects a plane extending through the first longitudinal axis at an oblique angle, whereby the exit orifice is positioned in the side wall such that the supplementary gas inlet, in use, directs a jet of gas through said exit orifice in the side wall of the gases passageway circumferentially along an interior surface of the gases passageway in order to generate helical flow along the interior surface of the gases passageway, such that the jet of gas follows a generally helical path towards the distal end of the gases passageway, wherein the helical flow along the interior surface of the gases passageway prevents mixing of the jet of gas with the principal flow of gases adjacent the exit orifice, but toward the distal end of the gases passageway, as momentum of the jet of gas decreases, the jet of gas mixes with the principal flow of gases in the gases passageway.

* * * * *